US008450089B2

(12) United States Patent
Ward et al.

(10) Patent No.: US 8,450,089 B2
(45) Date of Patent: May 28, 2013

(54) COMPOUNDS AS L-CYSTINE CRYSTALLIZATION INHIBITORS AND USES THEREOF

(75) Inventors: Michael D. Ward, New York, NY (US); Jeffrey D. Rimer, Houston, TX (US)

(73) Assignee: New York University, New York, NY (US)

( * ) Notice: Subject to any disclaimer, the term of this patent is extended or adjusted under 35 U.S.C. 154(b) by 261 days.

(21) Appl. No.: 12/953,096

(22) Filed: Nov. 23, 2010

(65) Prior Publication Data
US 2011/0177173 A1    Jul. 21, 2011

Related U.S. Application Data

(60) Provisional application No. 61/263,809, filed on Nov. 23, 2009.

(51) Int. Cl.
*A61K 38/05* (2006.01)
*A61K 31/21* (2006.01)
*A61K 31/225* (2006.01)
*A61K 31/22* (2006.01)
*C12P 13/12* (2006.01)

(52) U.S. Cl.
USPC ........ 435/113; 514/21.91; 514/891; 514/506; 514/547; 514/550; 514/551

(58) Field of Classification Search
USPC ............... 435/113; 514/21.91, 891, 506, 547, 514/550, 551
See application file for complete search history.

(56) References Cited

U.S. PATENT DOCUMENTS

| | | | | |
|---|---|---|---|---|
| 6,991,937 B2 * | 1/2006 | Asplin et al. | ..................... | 436/89 |
| 2007/0078093 A1 * | 4/2007 | Thoene | ........................... | 514/18 |

OTHER PUBLICATIONS

Dolin, DJ., et al., "Effect of Cystine-Binding Thiol Drugs on Urinary Dystine Capacity in Patients with Cystinuria," Journ of Endourology, vol. 19, No. 3, Apr. 2005, pp. 429-432.
Mattoo, A., et al., "Cystinuria," Seminars in Nephrology. vol. 28, No. 2, Mar. 2008, pp. 181-191.
Moe, Orson W., "Kidney stones: pathophysiology and medical management," Lancet 2006, vol. 367, pp. 333-344.
Becker, Gavin, "Cystine stones," Nephrology 2007; vol. 12, pp. S4-S10.
Nakagawa, Y., et al., "Clinical Use of Cystine Supersaturation Measurements," The Journal of Urology, vol. 164, Nov. 2000, pp. 1481-1485.
Moggach, S.A., et al., "The effect of pressure on the crystal structure of hexagonal l-cystine," Journal of Synchrotron Radiation (2005), 12, pp. 598-607, ISSN 0909-0495.
Dahaou, S., et al., "CCD Charge Density Study on Crystals with Large Unit Cell Parameters: The case of Hexagonal L-Cystine," J. Phys. Chem. A, 1999, vol. 103, pp. 6240-6250.
Girija, E.K., et al., "Crystallization of cystine," Journal of Materials Science: Materials in Medicine, vol. 6 (1995), pp. 617-619.
Fujiki, Y., et al., "Anisotropic Decoration of Gold Nanoparticles onto Specific Crystal Faces of Organic Single Crystals**," Angewandte Chemie Int. Ed., 2006, vol. 45, pp. 4764-4767.
Chaney, M.O., et al., "The Crystal and Molecular Structure of Tetragonal L-Cystine," Acta Cryst B, 1974, Mar. 15; B30: 711-716.
Steinrauf, L.K., et al., "The Cyrstal Structue of L-Cystine Hdrochloride," J. Amer. Chem. So., 1958; 80(15): 3835-3838.
Kominani, S., "X-Ray Diffractionand Electron Spin Resonance Studies of Single Crystals of Copper (II) Doped L-Systine Dihydrochloride Dihydrate," J. Phys. Chem., 1976, vol. 80, No. 2, pp. 203-210.
Carta, R., et al., "Solubilities of L-Cystine, L-Tyrosine, L-Leucine, and Glycine in Aqueous Solutions at Various pHs and NaCl Concentrations," J. Chem. Eng. Data, 1996: vol. 41, No. 3, pp. 414-417.
Kuzmenko, I., et al., "Formation of Chiral Interdigitated Multilayers at the Air-Liquid Interface Through Acid-Base Interactions," Science, vol. 274, Dec. 20, 1996, pp. 2046-2049.
Weinbach, S.P., et al., "Control of Structure and Growth of Polymorphic Crystalline Thin Films of Amphiphilic Molecules on Liquid Surfaces," Science, vol. 264, Jun. 10, 1994, pp. 1566-1570.
Graether, S.P., et al., "B-Helix Structure and ice-binding properties of a hyperactive antifreeze protein from an insect," Nature, vol. 406, Jul. 20, 2000, pp. 325-328.
Graham, L.A., et al., "Glycine-Rich Antifreeze Proteins from Snow Fleas," Science, vol. 310, Oct. 21, 2005, at p. 461.
Liou, Y., et al., "Mimicry of ice structure by surface hydroxyls and water of a B-helix antifreeze protein," Nature, vol. 406, Jul. 20, 2000, pp. 322-324.
Sonnichsen, F.D., et al., "The Nonhelical Structure of Antifreeze Protein Type III," Science, vol. 259, Feb. 19, 1993, pp. 1154-1157.
Weissbuch, I., et al., "Molecular Recognition at Crystal Interfaces," Articles, Aug. 9, 1991, pp. 637-645.
Orme, C.A., et al., "Formation of chiral morphologies through selective binding of amino acids to calcite surface steps," Nature, vol. 411, Jun. 14, 2001, pp. 775-779.
Stephenson, A.E., et al., "Peptides Enhance Magnesium Signature in Calcite: Insights into Origins of Vital Effects," Science, vol. 322, Otober 31, 2008, pp. 724-727.
Sheng, X., et al., "Adhesion at calcium oxalate crystal surfaces and the effect of urinary constituents," PNAS, Jan. 11, 2005, vol. 102, No. 2, pp. 267-272.
De Yoreo, J.J., et al., "Shaping Crystals and Biomolecules," Science 306, 1301 (2004; DOI: 10.1126/science.1100889.
Grohe, B., et al., "Control of Calcium Oxalate Crystal Growth by Face-Specific Adsorption of an Osteopontin Phosphopeptide," J. Am. Chem. Soc. 2007, vol. 129, pp. 14946-14951.
Sizemore, J.P., et al., "A New Model for the Effect of Molecular Imposters on the Shape of Faceted Molecular Crystals," Crystal Growth & Design, 2009, vol. 9, No. 6, pp. 2637-2645.

(Continued)

*Primary Examiner* — Abigail Fisher
(74) *Attorney, Agent, or Firm* — Klauber & Jackson LLC

(57) ABSTRACT

A method of preventing or inhibiting L-cystine crystallization using the compounds of formula I is disclosed.

$$R^{1a}\text{—O-(-A-L-)}_m\text{-A-O—}R^{1b} \qquad \text{I,}$$

wherein A, L, $R^{1a}$, $R^{1b}$, and m are as described herein. The compounds may be prepared as pharmaceutical compositions, and may be used for the prevention and treatment of conditions that are causally related to L-cystine crystallization, such as comprising (but not limited to) kidney stones.

31 Claims, 8 Drawing Sheets

OTHER PUBLICATIONS

Jung, T., et al., "Probing Crystallization of Calcium Oxalate Monohydrate and the Role of Macromolecule Additives with in Situ Atomic Force Microscopy," Langmuir, 2004, vol. 20, pp. 8587-8596.

Kessler, A., et al., "Antioxidant Effect of Cysteamine in Brain Cortex of Young Rats," Neurochem. Res. (2008) vol. 33, pp. 737-744.

Wilmer, M.J., et al., "Cystine Dimethylester Model of Cystinosis: Still Reliable?" Pediatric Research, vol. 62, No. 2, 2007, pp. 151-155.

Foreman, J.W., et al., "Effect of Cystine Dimethylester on Renal Solute Handling and Isolated Renal Tubule Transport in the Rat: A New Model of the Fanconi Syndrome," Metabolism, vol. 36, vol. 12, Dec. 1987, pp. 1185-1191.

Kallistratos, V.G., et al., "Experimentelle Untersuchungen zur Frage der chemischen Auflosung von Cystinsteinen," Arzneimittel-Forschung, 1972: vol. 22, No. 9, pp. 1434.

Konigsberger, E., et al., "Solubility of L-Cystine in NaCl and Artificial Urine Solutions," Monatschefte Fur Chemie, 2000; vol. 131, vol. 1, pp. 39-45.

Oughton, B.M., et al., "The Crystal Structure of Hexagonal L-Cystine," Acta Crystallographica, 1959, vol. 12, No. 5, pp. 396-404.

Vijayalakshmi, B.K., et al., "Crystal and Molecular Structue of L-Cystine Dimethyl Ester Dihydrochloride Monohydrate," Acta Cryst B, 1975; B31 (Apr. 15), pp. 993-998.

Eldjarn, L., et al., "The Rationale of Mixed Disulphides in the Treatment of Cystinuria," Scandinav. J. Clin. & Lab Investigation, vol. 16, 1964, pp. 153-164.

Theriault, Y., et al., "A nuclear magnetic resonance study of the equilibria and kinetics of the reaction of penicillamine with cystine and related disulfides," Canadian J. Chem, 1985; vol. 63, No. 8, pp. 2225-2231.

* cited by examiner 1.7 mg/L CDME     5.1 mg/L CDME     25.2 mg/L CDME

COMPOUNDS AS L-CYSTINE CRYSTALLIZATION INHIBITORS AND USES THEREOF

RELATED APPLICATION

The present application claims the benefit under 35 U.S.C. §119 of U.S. Provisional Application Ser. No. 61/263,809 filed Nov. 23, 2009. The contents of said provisional application is hereby incorporated by reference in its entirety.

GOVERNMENT RIGHTS

This invention was made in part with government support under Grant No. NIDDK R01-DK068551 awarded by the National Institute of Health. Accordingly, the United States Government has certain rights in the invention.

FIELD OF THE INVENTION

The present invention relates to the identification of compounds that inhibit L-cystine crystallization, and the use of such compounds and compositions thereof to prevent or slow L-cystine crystal production. This invention also relates to methods for preventing and/or treating conditions that are causally related to L-cystine crystallization, such as comprising (but not limited to) kidney stones, using the compounds of the invention. It is to be understood that such compounds may be used either alone or in combination with other compounds having the activity set forth herein.

BACKGROUND OF THE INVENTION

L-cystine stones account for less than 2% of adult kidney stones and affect more than 100,000 U.S. patients. L-cystine stones, which are larger and are more likely to cause chronic kidney disease than calcium oxalate monohydrate (COM) stones, form as a consequence of excessive levels of L-cystine in the urine due to defective reabsorption of filtered cystine [1]. This autosomal recessive disorder is caused by mutations in one of two genes coding for components of proximal renal tubule amino acid transporters. Affected genes are either SLC3A1 on chromosome 2 leading to type A cystinuria, or SLC7A9 on chromosome 19 leading to type B [2]. The low solubility of L-cystine [3] induces rapid crystallization, which is followed by aggregation to generate stones (FIG. 1A) with sizes that can achieve centimeter dimensions.

Current treatments include high fluid intake [4], increasing urine pH through ingestion of alkalinizing potassium or sodium salts [4, 5], or the administration of L-cystine binding thiol drugs (CBTDs), such as D-penicillamine (HS—C(CH$_3$)$_2$—CH(NH$_2$)—COOH) and α-mercaptopropionylglycine (α-MPG or tiopronin: HS—CHCH$_3$—CO—NH—CH$_2$—COOH), which undergo a thiol-disulfide exchange with L-cystine to generate more soluble products [1]. These treatments suppress, but often do not completely prevent, stone formation. Thiol drugs have an unpleasant odor and can cause adverse side-effects, such as nausea, fever, fatigue, and skin allergies [5]. CBTDs are accompanied by high fluid intake to achieve a cystine excretion rate of 2.9 mM/day (i.e. urine volumes of 3 L/day) [4] and thiol excretion rates of 0.5-6 mM/day. A shortcoming of thiol drugs, however, is their inadequacy to reduce and solubilize large enough quantities of L-cystine in the urine based on acceptable dosages (up to 2000 mg/day), which are limited due to hypersensitivity and toxicity concerns.

Therefore, there is a need for an improved method to prevent, inhibit or slow L-cystine crystal production, and it is toward the fulfillment of that need that the present invention is directed.

SUMMARY OF THE INVENTION

In a first aspect, the present invention relates to the prevention of L-cystine kidney stones based on crystal growth inhibition via the binding of tailored growth inhibitors to specific crystal surfaces through molecular recognition.

Thus, one aspect of the invention provides a method for preventing, inhibiting or slowing the growth of L-cystine crystallization comprising administering an effective amount of a compound of formula I:

or a pharmaceutically acceptable salt, solvate, cocrystal, or prodrug thereof, and stereoisomers, tautomers and isotopic variants thereof; and wherein
each A is

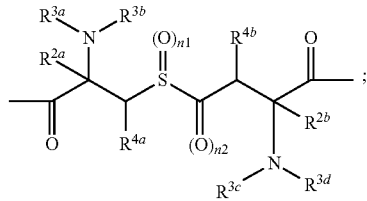

L is —O—C$_1$-C$_6$ alkylene-O—, —O-aryl-O—, or a group —O—(CH$_2$—CH$_2$—O—)$_t$—; the subscript t is 1-10; the subscript m is 0-10;
each R$^{1a}$ and R$^{1b}$ is independently selected from H, alkyl, alkenyl, alkynyl, aryl, aralkyl, and cycloalkyl;
each R$^{2a}$, R$^{2b}$, R$^{3a}$, R$^{3b}$, R$^{3c}$, R$^{3d}$, R$^{4a}$, and R$^{4b}$ is independently selected from H, and alkyl; and
each subscript n1 and n2 is independently 0, 1, or 2;
provided that when each n1 and n2 is 0, then at least one of R$^{1a}$ and R$^{1b}$ is other than H.

In one embodiment, with respect to formula I, subscript m is 1-5.

In one embodiment, with respect to formula I, L is —O—CH$_2$—O—. In another embodiment L is —O—CH$_2$—CH$_2$—O—.

In one embodiment, with respect to formula I, L is

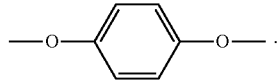

In one embodiment, with respect to formula I, L is —O—(CH$_2$—CH$_2$—O)$_t$—; and the subscript t is 1; In another embodiment the subscript t is 2.

In one embodiment, with respect to formula I, subscript m is 0.

In one embodiment, with respect to formula I, subscript m is 0; and the compound is according to formula II:

and wherein A, R$^{1a}$ and R$^{1b}$ are as described for formula I.

Another aspect of the invention provides a method for preventing inhibiting, or slowing the growth of L-cystine crystallization comprising administering an effective amount of a compound of formula I:

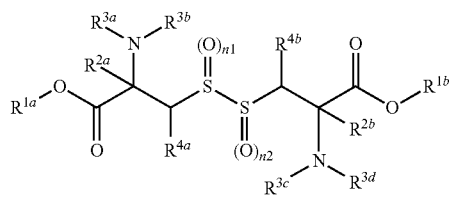

or a pharmaceutically acceptable salt, solvate, cocrystal, or prodrug thereof, and stereoisomers, tautomers and isotopic variants thereof; and wherein
each $R^{1a}$ and $R^{1b}$ is independently selected from H, alkyl, alkenyl, alkynyl, aryl, arylalkyl, and cycloalkyl;
each $R^{2a}$, $R^{2b}$, $R^{3a}$, $R^{3b}$, $R^{3c}$, $R^{3d}$, $R^{4a}$, and $R^{4b}$ is independently selected from H, and alkyl; and
each n1 and n2 is independently 0, 1, or 2;
provided that when each n1 and n2 is 0, then at least one of $R^{1a}$ and $R^{1b}$ is other than H.

In one particular embodiment of the invention, with respect to formula I, each of $R^{2a}$, $R^{2b}$, $R^{3a}$, $R^{3b}$, $R^{3c}$, $R^{3d}$, $R^{4a}$, and $R^{4b}$ is H.

In another particular embodiment of the invention, with respect to formula I, each of $R^{1a}$ and $R^{1b}$ is Me. In yet another embodiment, one of $R^{1a}$ and $R^{1b}$ is Me and the other is H.

In another particular embodiment of the invention, with respect to formula I, each of $R^{1a}$ and $R^{1b}$ is Et. In yet another embodiment, one of $R^{1a}$ and $R^{1b}$ is Et and the other is H.

In another particular embodiment of the invention, with respect to formula I, each of $R^{1a}$ and $R^{1b}$ is t-Bu. In yet another embodiment, one of $R^{1a}$ and $R^{1b}$ is t-Bu and the other is H.

In yet another particular embodiment of the invention, with respect to formula I, each n1 and n2 is 0.

Another aspect of the invention provides a pharmaceutical composition for preventing, inhibiting, or slowing the growth of L-cystine crystallization comprising a pharmaceutically acceptable carrier and a pharmaceutically effective amount of a compound according to formula I.

Yet another aspect of the invention provides a method for preventing, inhibiting or slowing growth of L-cystine kidney-stone formation in a subject in need thereof, the method comprising administering to the subject a pharmaceutically effective amount of a compound according to formula I.

Yet another aspect of the invention provides a method of treating a subject having chronic kidney disease, comprising administering to the subject a pharmaceutically effective amount of a compound according to formula I.

A further aspect of the invention provides a method for reducing a L-cystine crystal concentration in a human or animal comprising administering to a human or animal a pharmaceutically effective amount of a compound according to formula I.

A further aspect of the invention provides a method for treating a L-cystine crystal related condition in a human or animal comprising administering to a human or animal a pharmaceutically effective amount of a compound according to formula I.

A further aspect of the invention provides a combination to treat or prevent an L-cystine crystal-related condition, consisting of a compound according to formula I and another treatment or treatments, which may include high fluid intake or alkalinizing potassium or sodium salts.

In one embodiment, with respect to the above methods, the L-cystine related condition is cystinuria.

In one embodiment, with respect to the above methods, the L-cystine related condition is kidney stone disease.

In a further aspect, the present invention provides pharmaceutical compositions, comprising a compound or compounds of the invention, and a suitable biocompatible or bioinert carrier, excipient or diluent. In this aspect of the invention, pharmaceutical composition can comprise one or more of the compounds described herein. Moreover, the compounds of the present invention useful in pharmaceutical compositions and treatment methods disclosed herein, are all pharmaceutically acceptable as prepared and used.

In a further aspect, the present invention provides compositions comprising a combination of a compound of the invention with various compounds or agents that may have a like effect on L-cystine crystallization. In this aspect of the invention, the pharmaceutical composition can comprise one or more of the compounds described herein, individually or in combination with each other.

Other objects and advantages will become apparent to those skilled in the art from a consideration of the ensuing detailed description, which proceeds with reference to the following illustrative drawings.

Figure 11:
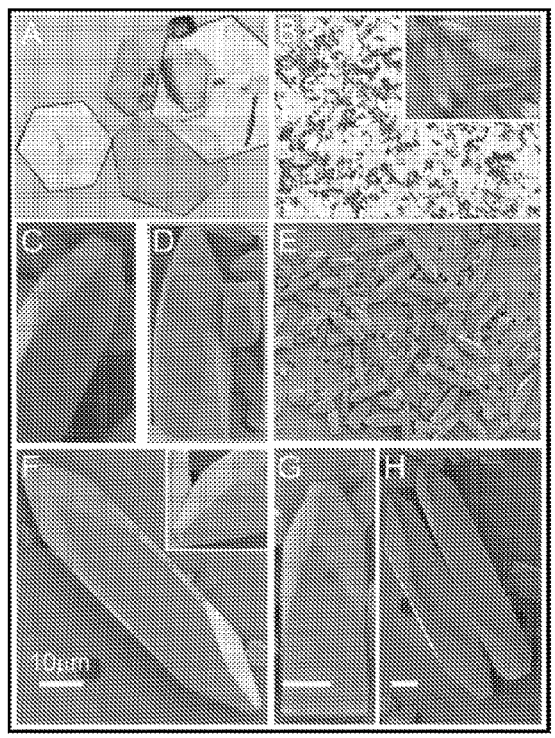

FIG. 11 depicts micrographs of L-cystine crystals crystallized in absence of growth inhibitors and in the presence of 5 mg/L CDME, at concentrations of 700 mg/L L-cystine. Micrographs of L-cystine crystals that were crystallized in the presence of 5 mg/L CDME and 700 mg/L L-cystine. (A) Optical micrograph of L-cystine hexagonal platelets grown in the absence of additive. (B) Optical micrograph of crystals grown in the presence of CDME at the same magnification (×10), with the inset image obtained at higher a magnification (×50). (C-H) SEM images highlighting variations in particle size, shape, and distribution in the presence of CDME. In these syntheses, there are small percentages of hexagonal needles and hexagonal platelets (with significantly reduced sizes compared to syntheses without CDME). Scale bars provided in (F-H) equal 10 μm.

Figure 12:
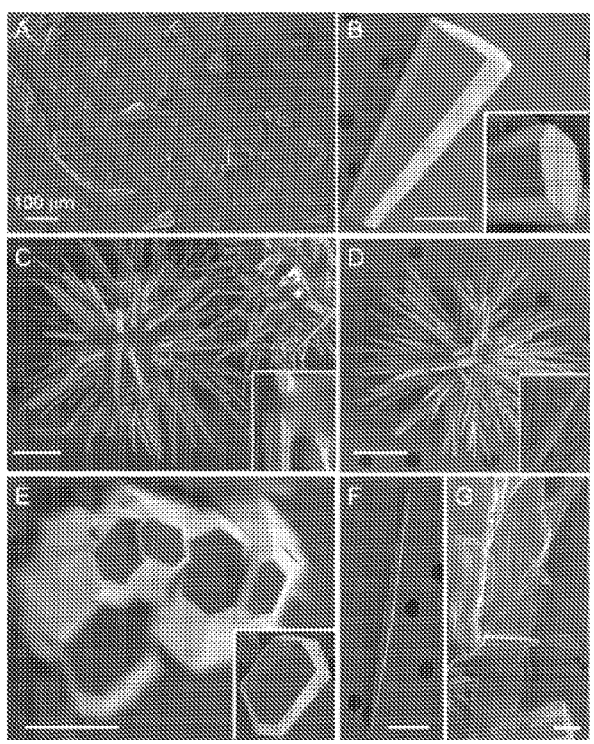

FIG. 12 depicts scanning electron micrographs of L-cystine crystals grown in the presence of CME. Scanning electron micrographs of L-cystine crystals grown in the presence of L-cystine methyl ester (CME) (scale bars=20 μm for images B-G). (A) A low magnification image capturing each of the five distinct morphologies that were observed in bulk crystallization experiments, which include (i) tapered hexagonal needles, (ii) "sea urchin-like" clusters of hexagonal needles, (iii) tapered hexagonal platelets, (iv) individual thin hexagonal needles, and (v) "amorphous-like" fibrils. (B) Image of tapered hexagonal needles that are the predominant morphology. (C,D) Images of sea urchin-like clusters with an amorphous core (C, inset) containing hundreds of tapered needles (D, inset) that protrude radially from the core. (E) Hexagonal platelets with (0001) basal surfaces and tapered {1010} sides. (F) Image of a thin needle that is thicker at the center and is tapered along axial directions toward each end of the crystal. (G) A fiber without distinct habit appears to be amorphous.

Figure 13:
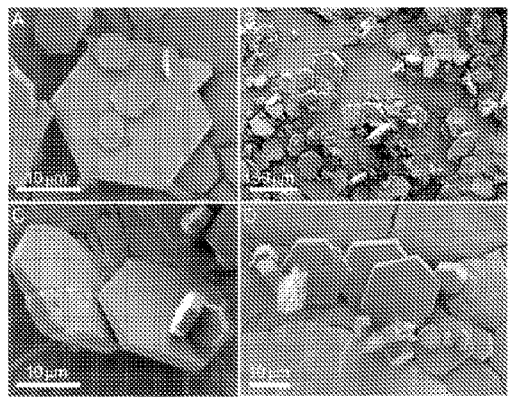

FIG. 13 depicts SEM images of L-cystine crystals crystallized in supersaturated L-cystine solutions containing L-cysteine. (A-D) SEM images of L-cystine crystals that were crystallized in supersaturated L-cystine solutions (700 mg/L) containing 10 mg/L of L-cysteine. Hexagonal L-cystine platelets crystallize in the presence of L-cysteine and exhibit sizes that range from 5 to 40 μm, which is significantly less than platelets with sizes of 100-400 μm generated in the absence of additive. Crystals were isolated from bulk solution by filtration using filters with 11 μm pores.

Figure 14:
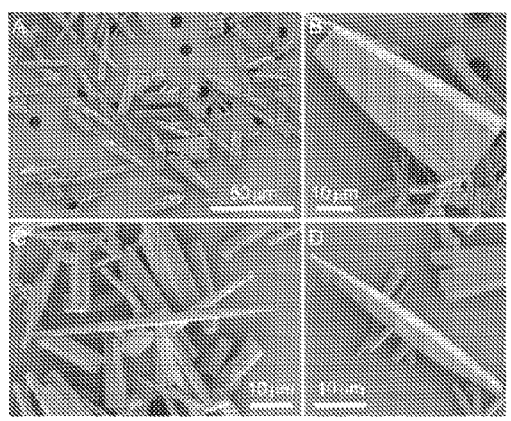

FIG. 14 depicts SEM images of L-cystine crystals that were crystallized in supersaturated L-cysteine solutions containing L-cysteine methylester. (A-D) SEM images of L-cystine crystals that were crystallized in supersaturated L-cystine solutions (700 mg/L) containing 10 mg/L of L-cysteine methylester. The growth inhibitor, which has a molecular structure that is one-half that of CDME, binds to {1010} faces of L-cystine crystals and alters the morphology from hexagonal platelets (in the absence of additive) to needles with lengths that are <50 μm and widths that are <5 μm. Crystals were isolated from bulk solution by filtration using filters with 8 μm pores.

Figure 15:
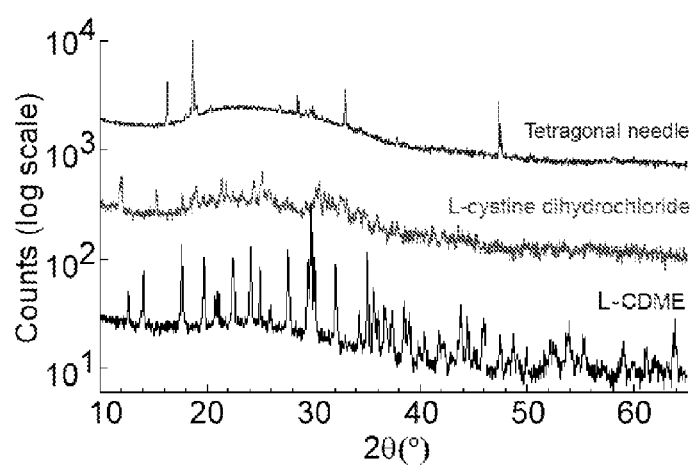

FIG. 15 depicts a comparison of powder X-ray diffraction patterns of the tetragonal form of L-cystine, L-cystine dihydrochloride, and CDME. Comparison of powder X-ray diffraction patterns of, L-cystine tetragonal needles, L-cystine dimethyl ester (CDME), and L-cystine dihydrochloride. A background measurement of the holder reveals that the broad increase in scattered intensity over the range $2\theta=15\text{-}40$ degrees is attributed to an amorphous peak from the glass holder. The counts are plotted on a log scale and offset vertically to separate data for improved visual comparison.

Figure 16:
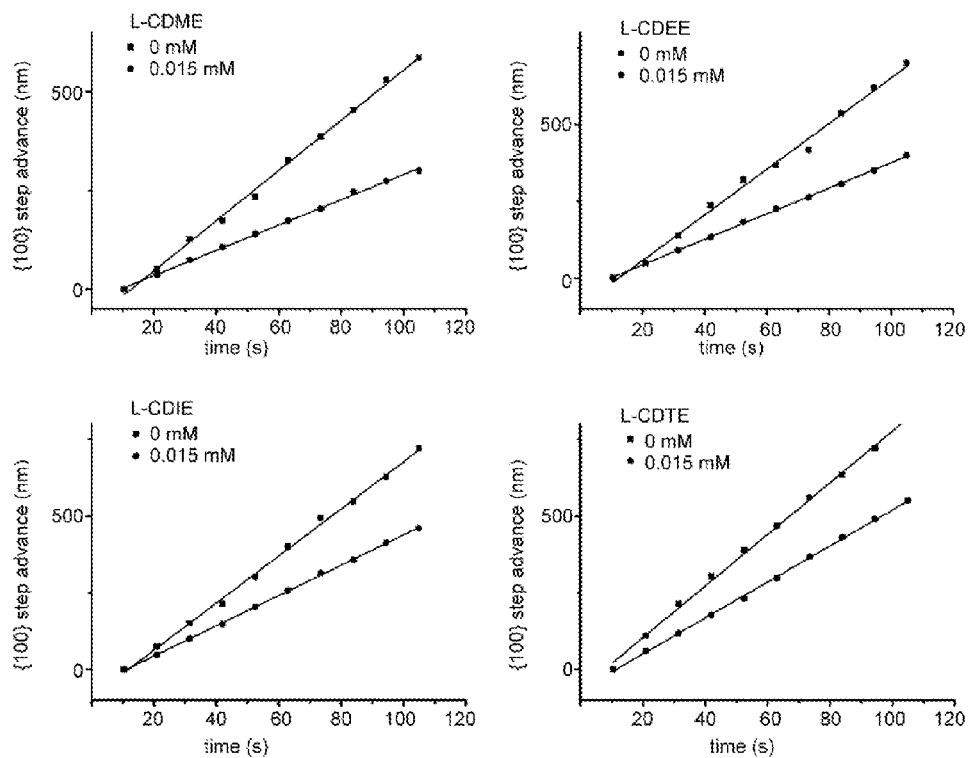

FIG. 16 depicts a comparison of the step velocities (from the slope of the step advancement dependence on time) for L-cystine crystal hillocks in the absence of inhibitor and after addition of 0.015 M inhibitor, for four different L-cystine diesters, CDME is the best inhibitor among these four compounds, and the inhibition effectiveness decreases with the size of the ester group.

Figure 17:
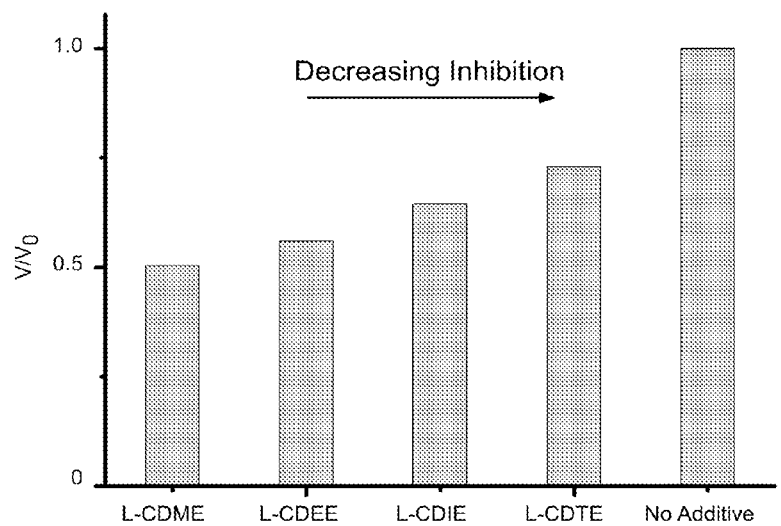

FIG. 17 depicts a comparison of the step velocities measured in the presence of the various diester inhibitors and in the absence of inhibitor. Inhibition is inversely related to the step velocity.

Figure 18:
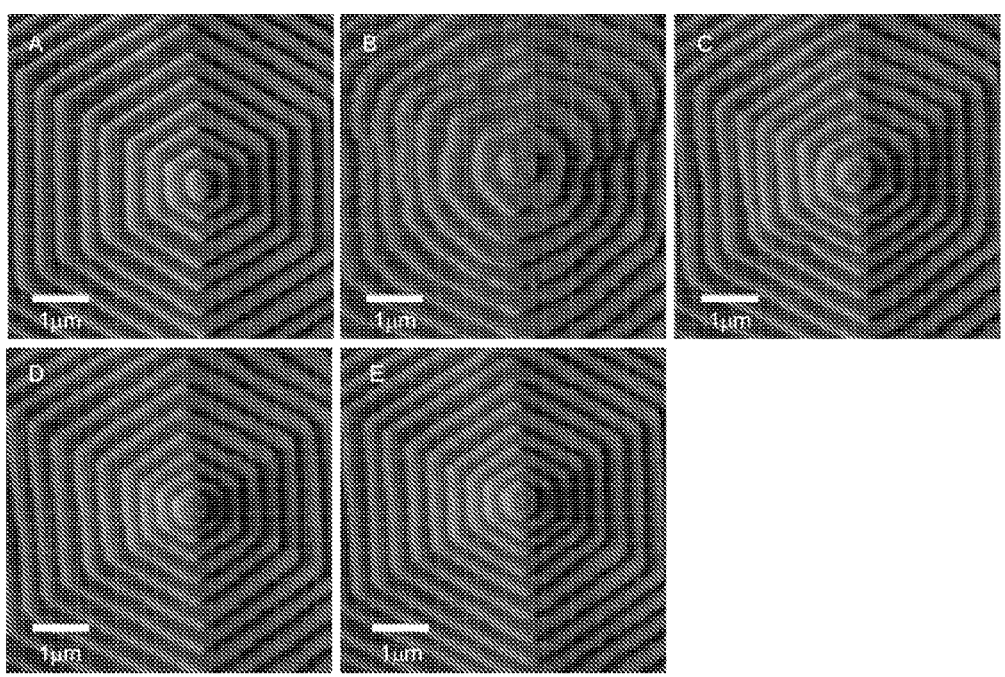

FIG. 18 depicts a comparison Images of the hexagonal hillocks on the L-cystine (001) face in an aqueous medium containing 2 mM L-cystine (A) without inhibitor and in the presence of (B) 0.015 mM L-CDME. (C) 0.015 mM L-CDEE (D) 0.015 mM L-CDIE (E) 0.015 mM L-CDTE. The greater degree of step roughening for L-CDME is a signature of its greater inhibition effect. The roughening decreases in the order L-CDME>L-CDEE>L-CDIE>L-CDTE, corresponding to the trend in the inhibition in FIG. 16.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

"Acyl" refers to a group or radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a group or radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group or radical —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)R$^{26}$ where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—CH≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —$N(H)OR^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —$S(O)_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —$S(O)R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —$SR^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —$NH_2$.

"Substituted amino" includes those groups recited in the definition of "substituted" herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group.

"Aminocarbonyl" refers to the group —$C(O)NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}C(O)NR^{38}R^{38}$ where each $R^{38}$ is independently hydrogen, alkyl, aryl or cycloalkyl, or where two R groups are joined to form an alkylene group.

"Aminocarbonyloxy" refers to the group —$OC(O)NR^{39}R^{39}$ where each $R^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —$NHR^{40}$ where $R^{40}$ represents an aryl group as defined herein.

"Aryloxycarbonyl" refers to a radical —C(O)—O-aryl where aryl is as defined herein.

"Arylsulfonyl" refers to a radical —$S(O)_2R^{41}$ where $R^{41}$ is an aryl or heteroaryl group as defined herein.

"Azido" refers to the radical —$N_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —$C(O)N(R^{42})_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Cycloalkoxy" refers to the group —$OR^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

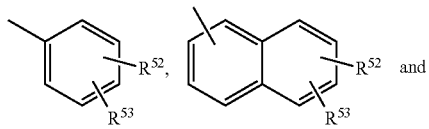

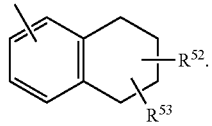

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$.NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

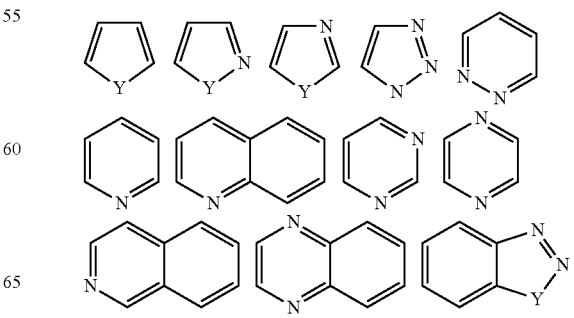

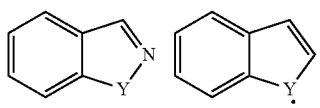

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

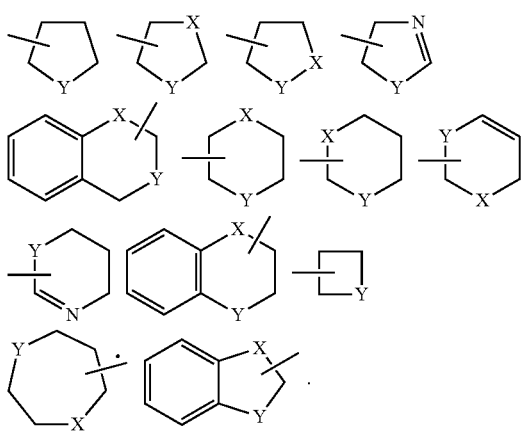

wherein each X is selected from CR$^{58}$, CR$^{58}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

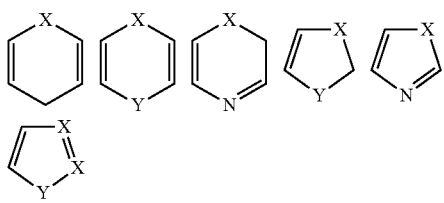

wherein each X is selected from CR$^{58}$, CR$^{58}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

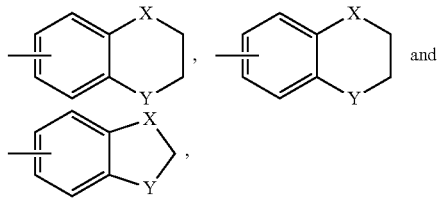

wherein each X is selected from CR$^{58}_2$, NR$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on the ring or rings of the compounds of this invention, or that may be present as a substituent in any "substituted" aryl and aliphatic groups present in the compounds.

Examples of hetero substituents include:
-halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$ wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}$$_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

As used herein, "mammal" refers to any member of the higher vertebrate animals comprising the class Mammalia, which includes, but is not limited to, humans.

As used herein, an "amount effective" shall mean an amount sufficient to cover the region of skin, hair, fur, or wool surface where a change in pigmentation is desired.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and/or that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease or a condition, is sufficient to effect such treatment for the disease or condition. The "therapeutically effective amount" can vary depending on the compound, the disease or condition and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or composition of the invention for cosmetic purposes.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

L-Cystine Stones and L-Cystine Crystallization

Figure 1:
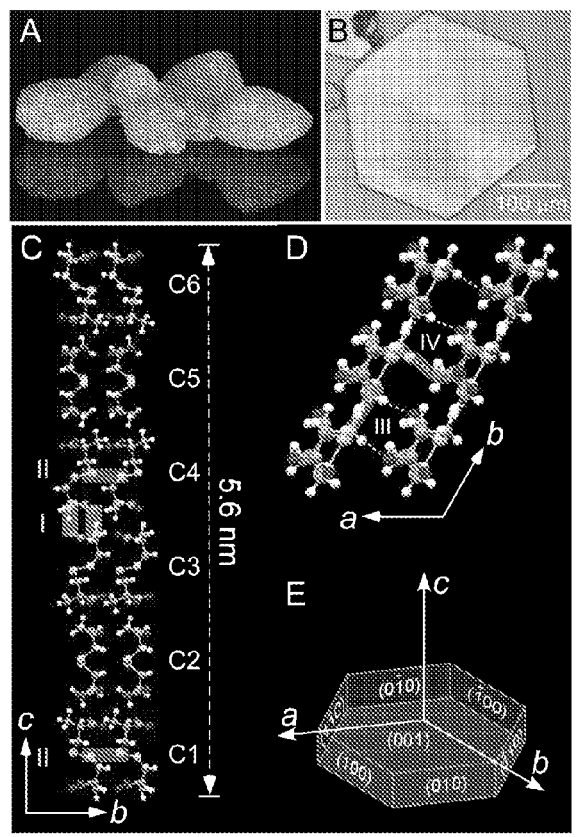
FIG. 1 depicts the hierarchical structure of L-cystine kidney stones, including the typical hexagonal platelet crystal habit formed in the absence of growth inhibitors.
(A) Human stones with millimeter-scale dimensions (courtesy of M. Lewis, International Cystinuria Foundation). (B) A hexagonal L-cystine crystal prepared in vitro. The faint lines on the top surface of the crystal, parallel to the edges, are the {100} steps. (C) Two adjacent helices of L-cystine molecules, viewed on the (100) plane, each winding about a $6_1$ screw axis that coincides with the c axis. Six L-cystine molecules, denoted C1 to C6, span the 5.6 nm c axis. Key intermolecular interactions include amine-carboxylate hydrogen bonds along the helix (I, $d_{N \ldots O}$=2.87 Å) and S . . . S interactions (II, $d_{S \ldots S}$=3.47 Å) between helices at intervals of c/2, depicted here for C1 and C4 along the [010] direction (identical S . . . S interactions occur at symmetry-related sites along the other five equivalent directions). (D) Intermolecular amine-carboxylate hydrogen bonds in the (001) plane (III, $d_{N \ldots O}$=2.79 Å; IV, $d_{N \ldots O}$=2.81 Å). Atom color code: carbon (gray), oxygen (red), nitrogen (blue), sulfur (yellow), hydrogen (white). (E) Schematic illustration of a hexagonal L-cystine crystal, with Miller indices. The six planes flanking (001) belong to the {100} family.

L-cystine stones are polycrystalline aggregates of individual crystals with well-defined hexagonal habit (FIG. 1), which crystallize in the hexagonal $P6_122$ space group ($C_6H_{14}N_2O_4S_2$) [6]. L-cystine molecules in the crystal structure exhibit intramolecular sulfur-amine H-bonding (FIG. 1C, I), and are associated through intermolecular sulfur-sulfur interactions (FIG. 1C, II) [7] and intermolecular amine-carboxylate H-bonding (FIG. 1D, III-VI). L-cystine crystals exhibit a hexagonal morphology (FIG. 1E), with a large (0001) basal surface (typical width=50-400 μm) and six equivalent {1010} faces (typical thickness ~10 μm).

Figure 2:
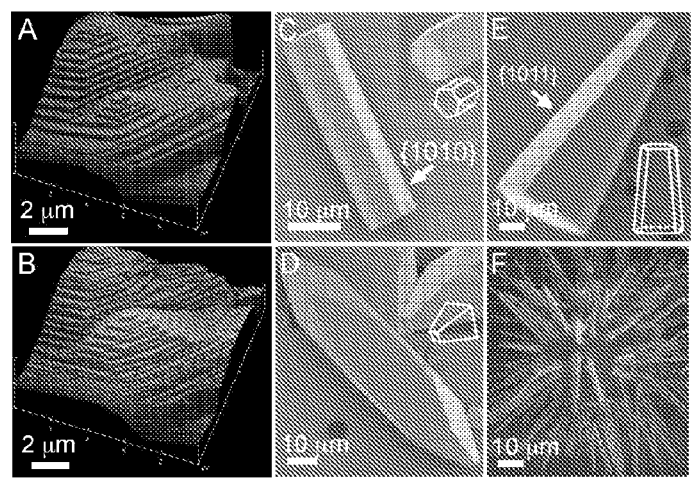
FIG. 2 depicts atomic force microscopy images of a cystine crystal surface hexagonal platelets and cystine crystals grown in the presence of growth inhibitors CDME and CME. (A, B) AFM images of a typical cystine crystal in an aqueous medium containing 2 mM L-cystine (relative supersaturation σ=5) acquired 12 minutes apart, revealing step advancement from hexagonal hillocks produced from two neighboring dislocations, consistent with the hexagonal habit in FIG. 1B. (C) In the presence of CDME and CME (5 mg/L) the L-cystine crystals exhibit a hexagonal needle-like habit with prominent {1010} faces and high c/a aspect ratios, as high as 30 for many crystals. (D) Crystallization in the presence of high concentrations of CDME also produces the tetragonal $P4_1$ polymorph, which is evident from the tapered end terminated with a square (001) face. (E) Crystallization in the presence of CME produces tapered, hexagonal needles with {1011}. The needles initially grow from a spherical mass that appears amorphous.
Figure 7:
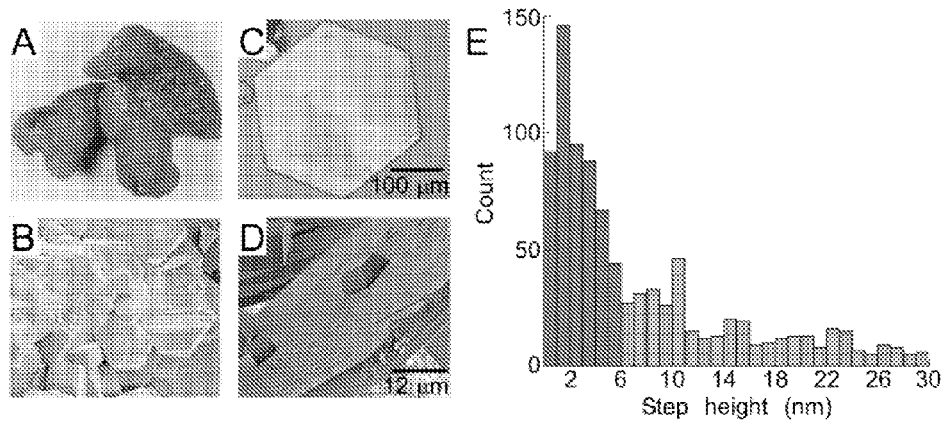
FIG. 7 depicts images of L-cystine kidney stones from human patients, hexagonal crystals generated in vitro, and a histogram of the step heights on multiple L-cystine crystals, as measured by atomic force microscopy.
(A-D) Images of L-cystine kidney stones from human patients and hexagonal crystals generated in vitro. (A) A photograph of an L-cystine stone was obtained with permission from Herring Laboratory (www.herringlab.com). (B) An SEM image reveals that L-cystine stones are polycrystalline aggregates of individual hexagonal crystals (image obtained from Herring Lab; www.herringlab.com). (C) The presence of steps on the (0001) surface of hexagonal crystals are clearly visible by optical microscopy. (D) An SEM image of a hexagonal L-cystine crystal reveal steps and a plate thickness of ~10 μm. (E) The distribution of step heights on multiple hexagonal crystals (~2000 steps) were measured by AFM topographical images. Steps range in height from a single L-cystine molecule in length (0.9±0.3 nm) to step bunches with heights up to 100 nm. The histogram, binned in 1-nm intervals corresponding to the length of an L-cystine molecule, reveals a significant percentage of steps with heights less than a unit cell (<5.7 nm, highlighted region).

L-cystine can be crystallized in vitro by slow evaporation [7], precipitation by pH neutralization of basic L-cystine solutions [8], or recrystallization by gradual cooling of supersaturated L-cystine [9]. Crystallization in basic (pH>8) and acidic solutions (pH<1) solutions generate tetragonal ($C_6H_{12}N_2O_4S_2$) [10] and monoclinic ($C_6H_{14}N_2O_4S_2^{2+}$·2Cl$^-$ and $C_6H_{14}N_2O_4S_2^{2+}$·2Cl$^-$·2H$_2$O) [11, 12] crystals, respectively. Crystallization at pH ~1 generates hexagonal platelets ($C_6H_{12}N_2O_4S_2$) with roughened (0001) surfaces [9], while solutions at physiological pH (pH 6-8) yield hexagonal crystals of L-cystine with a basal surface decorated with terraces which are bound by steps corresponding to {1010} crystal planes. Steps originate from screw dislocations at the center of the hexagonal plate and advance in a spiral growth pattern to generate pyramidal (0001) surfaces with a distribution of step heights that range from 1 nm to 100-nm step bunches (FIGS. 2A, 2B and 7). A large number of steps are observed with heights less than or equal to a single unit cell length along the c-axis (5.7 nm).

The terraced surfaces of L-cystine crystals provide an ideal interface for measuring crystal growth by real time in situ atomic force microscopy (AFM), using successive images to measure the rate of step advancement across the frame. AFM studies reveal that the L-cystine concentration must be adjusted to 2 mM, which is five times larger than L-cystine solubility at room temperature [13], to achieve growth rates within a reasonable measurement timeframe. The velocity was obtained by linear regression of step advancement with increasing time (FIG. 2A). In an typical measurement, hexagonal {1010} steps advance at a velocity of 29±4 nm/min, independent of step height, as revealed by AFM topographical images that capture the progression of step growth at periodic time intervals (FIGS. 2B and 2C).

As set forth later herein, L-cystine crystallization has been investigated in the presence of tailored growth inhibitors, which can tune crystal properties, such as habit, chirality, and polymorphism [14, 15], by binding to specific crystallographic faces and altering the kinetics of growth unit attachment. Hexagonal L-cystine is ideally suited for tailored growth inhibition, wherein an additive with molecular recognition for binding to structurally-equivalent {1010} faces can inhibit growth along six directions. Past studies have established that inhibitors consisting of two components, a binder moiety exhibiting molecular recognition for docking to the crystal surface and a perturber moiety hindering attachment of crystal growth units, influence crystallization of amino acids, such as glycine and alanine [16]. Growth inhibitors may be structural mimics of the crystal or additives that strongly interact with crystal surfaces, such as antifreeze proteins (AFPs) that suppress ice nucleation [17-20] or peptides, proteins, and ions that influence biomineral formation (e.g. $CaCO_3$ bone [21, 22] and calcium oxalate kidney stones [23-25]).

Crystal growth is commonly described by a terrace-ledge-kink model, wherein steps propagate across the surface by the addition of solute molecules to kink sites. Steps originating from screw dislocations exhibit a spiral growth pattern where the first turn occurs once the step reaches a critical length [26]. As such, growth inhibitor binding to step surfaces can increase the length of step edges, which decreases growth perpendicular to the crystal face, or can suppress step growth rates by binding to ledge sites and "pinning" step propagation.

The Compounds

As described herein, the present invention relates to the prevention of L-cystine kidney stones based on crystal growth inhibition via the binding of tailored growth inhibitors to specific crystal surfaces through molecular recognition. Bulk crystallization and in situ atomic force microscopy (AFM) growth studies in real time indicate that two structural mimics of L-cystine, L-cystine dimethylester (CDME) and L-cystine methylester (CME), substantially inhibit the rate of crystal growth, reduce crystal yield, and significantly alter crystal habit from hexagonal platelets to needles, suggesting a new strategy for the prevention of cystinuria.

Thus, one aspect of the invention provides a method for preventing inhibiting, or slowing the growth of L-cystine crystallization comprising administering an effective amount of a compound of formula I:

or a pharmaceutically acceptable salt, solvate, cocrystal, or prodrug thereof, and stereoisomers, tautomers and isotopic variants thereof; and wherein
each A is

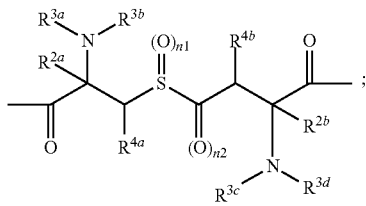

L is —O—$C_1$-$C_6$ alkylene-O—, —O-aryl-O—, or a group —O—($CH_2$—$CH_2$—O—)$_t$—; the subscript t is 1-10; the subscript m is 0-10;
each $R^{1a}$ and $R^{1b}$ is independently selected from H, alkyl, alkenyl, alkynyl, aryl, aralkyl, and cycloalkyl;
each $R^{2a}$, $R^{2b}$, $R^{3a}$, $R^{3b}$, $R^{3c}$, $R^{3d}$, $R^{4a}$, and $R^{4b}$ is independently selected from H, and alkyl; and
each subscript n1 and n2 is independently 0, 1, or 2;
provided that when each n1 and n2 is 0, then at least one of $R^{1a}$ and $R^{1b}$ is other than H.

In one embodiment, with respect to formula I, the subscript m is 1-5.

In one embodiment, with respect to formula I, L is —O—$CH_2$—O—. In another embodiment L is —O—$CH_2$—$CH_2$—O—.

In one embodiment, with respect to formula I, L is

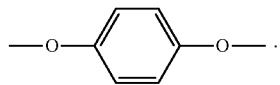

In one embodiment, with respect to formula I, L is —O—($CH_2$—$CH_2$—O)$_t$—; and the subscript t is 1; In another embodiment the subscript t is 2.

In one embodiment, with respect to formula I, subscript m is 0.

In one embodiment, with respect to formula I, the subscript m is 0; and the compound is according to formula II:

$R^{1a}$—O-A-O—$R^{1b}$  II;

and wherein A, $R^{1a}$ and $R^{1b}$ are as described for formula I.

Another aspect of the invention provides a method for preventing, inhibiting or slowing the growth of L-cystine crystallization comprising administering an effective amount of a compound of formula III:

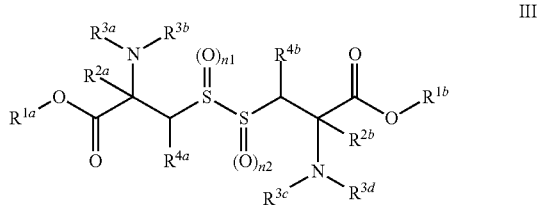

or a pharmaceutically acceptable salt, solvate, cocrystal, or prodrug thereof, and stereoisomers, tautomers and isotopic variants thereof; and wherein
each $R^{1a}$ and $R^{1b}$ is independently selected from H, alkyl, alkenyl, alkynyl, aryl, arylalkyl, and cycloalkyl;
each $R^{2a}$, $R^{2b}$, $R^{3a}$, $R^{3b}$, $R^{3c}$, $R^{3d}$, $R^{4a}$, and $R^{4b}$ is independently selected from H, and alkyl; and
each n1 and n2 is independently 0, 1, or 2;
provided that when each n1 and n2 is 0, then at least one of $R^{1a}$ and $R^{1b}$ is other than H.

In one embodiment of the invention, with respect to formula I, II or III, each of $R^{2a}$ and $R^{2b}$ is H.

In another embodiment of the invention, with respect to formula I, II or III, one of $R^{2a}$ and $R^{2b}$ is H; and the other is alkyl.

In another embodiment of the invention, with respect to formula I, II or III, one of $R^{2a}$ and $R^{2b}$ is H; and the other is Me, Et, i-Pr, n-Pr, or n-Bu.

In another embodiment of the invention, with respect to formula I, II or III, each of $R^{2a}$ and $R^{2b}$ is alkyl.

In another embodiment of the invention, with respect to formula I, II or III, each of $R^{2a}$ and $R^{2b}$ is Me, Et, i-Pr, n-Pr, or n-Bu.

In one particular embodiment of the invention, with respect to formula I, II or III, each of $R^{2a}$ and $R^{2b}$ is Me.

In one embodiment of the invention, with respect to formula I, each of $R^{3a}$ and $R^{3b}$ is H.

In another embodiment of the invention, with respect to formula I, II or III, one of $R^{3a}$ and $R^{3b}$ is H; and the other is alkyl.

In another embodiment of the invention, with respect to formula I, II or III, one of $R^{3a}$ and $R^{3b}$ is H; and the other is Me, Et, i-Pr, n-Pr, or n-Bu.

In another embodiment of the invention, with respect to formula I, II or III, each of $R^{3a}$ and $R^{3b}$ is alkyl.

In another embodiment of the invention, with respect to formula I, II or III, each of $R^{3a}$ and $R^{3b}$ is Me, Et, i-Pr, n-Pr, or n-Bu.

In another embodiment of the invention, with respect to formula I, II or III, each of $R^{3a}$ and $R^{3b}$ is Me.

In one embodiment of the invention, with respect to formula I, II or III, each of $R^{3c}$ and $R^{3d}$ is H.

In another embodiment of the invention, with respect to formula I, II or III, one of $R^{3c}$ and $R^{3d}$ is H; and the other is alkyl.

In another embodiment of the invention, with respect to formula I, II or III, one of $R^{3c}$ and $R^{3d}$ is H; and the other is Me, Et, i-Pr, n-Pr, or n-Bu.

In another embodiment of the invention, with respect to formula I, II or III, each of $R^{3c}$ and $R^{3d}$ is alkyl.

In another embodiment of the invention, with respect to formula I, II or III, each of $R^{3c}$ and $R^{3d}$ is Me, Et, i-Pr, n-Pr, or n-Bu.

In another embodiment of the invention, with respect to formula I, II or III, each of $R^{3c}$ and $R^{3d}$ is Me.

In one embodiment of the invention, with respect to formula I, II or III, each of $R^{4a}$ and $R^{4b}$ is H.

In another embodiment of the invention, with respect to formula I, II or III, one of $R^{4a}$ and $R^{4b}$ is H; and the other is alkyl.

In another embodiment of the invention, with respect to formula I, one of $R^{4a}$ and $R^{4b}$ is H; and the other is Me, Et, i-Pr, n-Pr, or n-Bu.

In another embodiment of the invention, with respect to formula I, II or III, each of $R^{4a}$ and $R^{4b}$ is alkyl.

In another embodiment of the invention, with respect to formula I, II or III, each of $R^{4a}$ and $R^{4b}$ is Me, Et, i-Pr, n-Pr, or n-Bu.

In another embodiment of the invention, with respect to formula I, II or III, each of $R^{4a}$ and $R^{4b}$ is Me.

In one embodiment of the invention, with respect to formula I, the compound is according to formula IVa, IVb, or IVc:

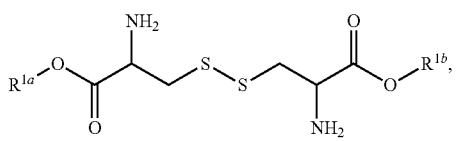

IVa

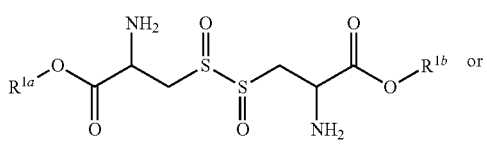

IVb

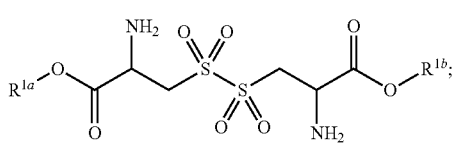

IVc and wherein $R^{1a}$ and $R^{1b}$ are as with respect to formula I.

In one particular embodiment of the invention, with respect to formula I, the compound is according to formula Va, Vb, Vc, or Vd:

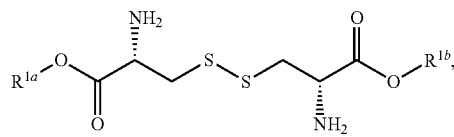

Va

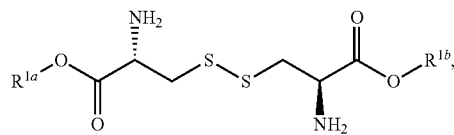

Vb

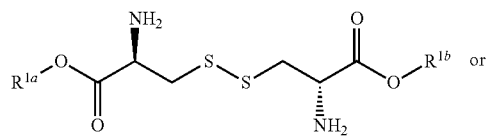

Vc or

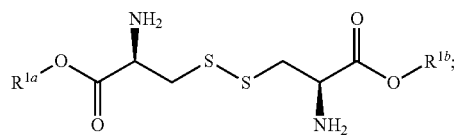

Vd and wherein $R^{1a}$ and $R^{1b}$ are as with respect to formula I.

In one embodiment of the invention, with respect to formula IVa-Vd, one of $R^{1a}$ and $R^{1b}$ is H; and the other is alkyl.

In another embodiment of the invention, with respect to formula IVa-Vd, one of $R^{1a}$ and $R^{1b}$ is H; and the other is Me, Et, n-Pr, i-Pr, n-Bu, or t-Bu.

In another embodiment of the invention, with respect to formula IVa-Vd, one of $R^{1a}$ and $R^{1b}$ is H; and the other is alkenyl.

In another embodiment of the invention, with respect to formula IVa-Vd, one of $R^{1a}$ and $R^{1b}$ is H; and the other is alkynyl.

In another embodiment of the invention, with respect to formula IVa-Vd, one of $R^{1a}$ and $R^{1b}$ is H; and the other is propargyl.

In another embodiment of the invention, with respect to formula IVa-Vd, one of $R^{1a}$ and $R^{1b}$ is H; and the other is cycloalkyl.

In another embodiment of the invention, with respect to formula IVa-Vd, one of $R^{1a}$ and $R^{1b}$ is H; and the other is cyclohexyl, cyclopentyl, cyclobutyl, or cyclopropyl.

In another embodiment of the invention, with respect to formula IVa-Vd, one of $R^{1a}$ and $R^{1b}$ is H; and the other is Me, Et, or cyclopropyl.

In another embodiment of the invention, with respect to formula IVa-Vd, each of $R^{1a}$ and $R^{1b}$ is alkyl.

In another embodiment of the invention, with respect to formula IVa-Vd, each of $R^{1a}$ and $R^{1b}$ is Me, Et, n-Pr, i-Pr, n-Bu, or t-Bu.

In another embodiment of the invention, with respect to formula IVa-Vd, each of $R^{1a}$ and $R^{1b}$ is alkenyl.

In another embodiment of the invention, with respect to formula IVa-Vd, each of $R^{1a}$ and $R^{1b}$ is alkynyl.

In another embodiment of the invention, with respect to formula IVa-Vd, each of $R^{1a}$ and $R^{1b}$ is propargyl.

In another embodiment of the invention, with respect to formula IVa-Vd, each of $R^{1a}$ and $R^{1b}$ is cycloalkyl.

In another embodiment of the invention, with respect to formula IVa-Vd, each of $R^{1a}$ and $R^{1b}$ is cyclohexyl, cyclopentyl, cyclobutyl, or cyclopropyl.

In another embodiment of the invention, with respect to formula IVa-Vd, each of $R^{1a}$ and $R^{1b}$ is Me, Et, or cyclopropyl.

In one particular embodiment of the invention, with respect to formula IVa-Vd, each of $R^{1a}$ and $R^{1b}$ is Me.

In another particular embodiment of the invention, with respect to formula I-Vd, each of $R^{1a}$ and $R^{1b}$ is Et. In yet another embodiment, one of $R^{1a}$ and $R^{1b}$ is Et and the other is H.

In another particular embodiment of the invention, with respect to formula I-Vd, each of $R^{1a}$ and $R^{1b}$ is t-Bu. In yet another embodiment, one of $R^{1a}$ and $R^{1b}$ is t-Bu and the other is H.

In one embodiment of the invention, with respect to formula I, the compound is according to formula VIa, VIb, VIc, VId, VIe, VIf, or VIg:

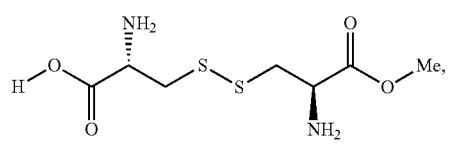
VIa

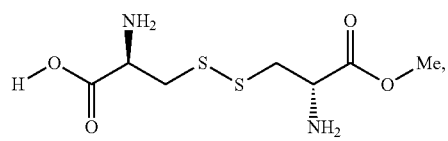
VIb

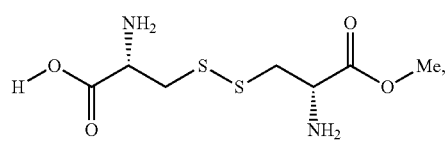
VIc

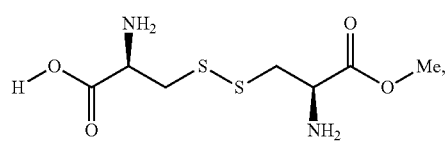
VId

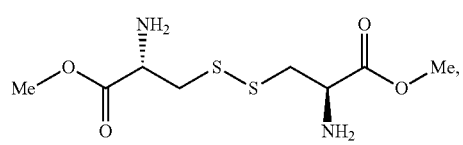
VIe

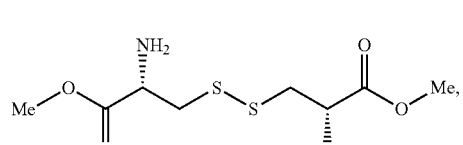
VIf or

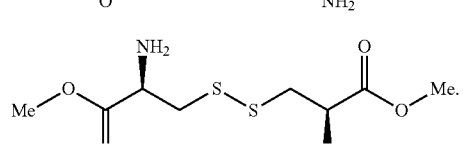
VIg

In one particular embodiment of the invention, the compound is according to formula VIa.

In another particular embodiment of the invention, the compound is according to formula VIb.

In another particular embodiment of the invention, the compound is according to formula VIc.

In another particular embodiment of the invention, the compound is according to formula VId.

In another particular embodiment of the invention, the compound is according to formula VIe.

In another particular embodiment of the invention, the compound is according to formula VIf.

In another particular embodiment of the invention, the compound is according to formula VIg.

In one preferred embodiment of the invention, the compound is L-cystine dimethylester (CDME).

In another preferred embodiment of the invention, the compound is L-cystine methylester (CME)

Another aspect of the invention provides a method for preventing, inhibiting or slowing the growth of L-cystine crystallization comprising administering an effective amount of cystamine.

In one embodiment, the compound is of formula VII:

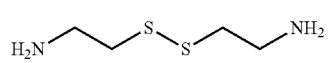
VII or a pharmaceutically acceptable salt, solvate, cocrystal, or prodrug thereof, and stereoisomers, tautomers and isotopic variants thereof.

In one embodiment of the invention, with respect to formula I, the compound is according to formula VIII:

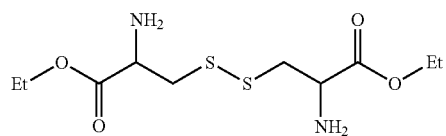
VIII or a pharmaceutically acceptable salt, solvate, cocrystal, or prodrug thereof, and stereoisomers, tautomers and isotopic variants thereof.

In one embodiment of the invention, with respect to formula I, the compound is according to formula IXa, IXb, IXc, IXd, IXe, IXf, or IXg:

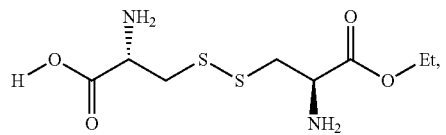
IXa

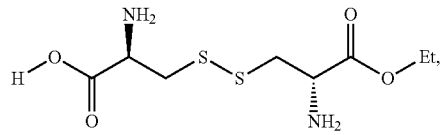
IXb

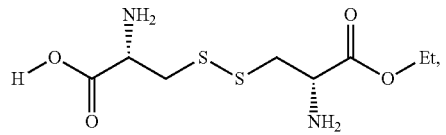
IXc

-continued

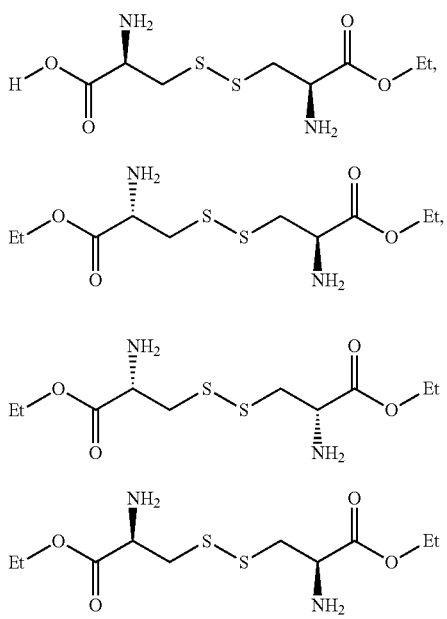

or a pharmaceutically acceptable salt, solvate, cocrystal, or prodrug thereof, and stereoisomers, tautomers and isotopic variants thereof.

In one particular embodiment of the invention, with respect to formula I, the compound is according to formula VIIId, VIIIg, IXd, or IXg:

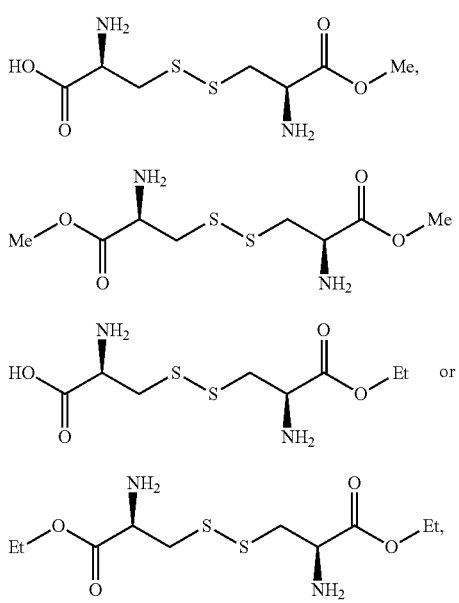

or a pharmaceutically acceptable salt, solvate, cocrystal, or prodrug thereof, and stereoisomers, tautomers and isotopic variants thereof.

In more particular embodiment of the invention, with respect to formula I, the compound is according to formula VIIId.

In more particular embodiment of the invention, with respect to formula I, the compound is according to formula VIIIg.

In more particular embodiment of the invention, with respect to formula I, the compound is according to formula IXd.

In more particular embodiment of the invention, with respect to formula I, the compound is according to formula IXg.

Another aspect of the invention provides a pharmaceutical composition for preventing, inhibiting, or slowing the growth of L-cystine crystallization comprising a pharmaceutically acceptable carrier and a pharmaceutically effective amount of a compound according to formula I, II, III, IVa-IVc, Va-Vd, VIa-VIg, VII, VIIIa-VIIIg, or IXa-IXg.

Yet another aspect of the invention provides a method for preventing, inhibiting or slowing growth of L-cystine kidney-stone formation in a subject in need thereof, the method comprising administering to the subject a pharmaceutically effective amount of a compound according to formula I, II, III, IVa-IVc, Va-Vd, VIa-VIg, VII, VIIIa-VIIIg, or IXa-IXg.

Yet another aspect of the invention provides a method of treating a subject having chronic kidney disease, comprising administering to the subject a pharmaceutically effective amount of a compound according to formula I, II, III, IVa-IVc, Va-Vd, VIa-VIg, VII, VIIIa-VIIIg, or IXa-IXg.

In one embodiment, with respect to the above methods, the subject is human.

A further aspect of the invention provides a method for reducing a L-cystine crystal concentration in a human or animal comprising administering to a human or animal a pharmaceutically effective amount of a compound according to formula I, II, III, IVa-IVc, Va-Vd, VIa-VIg, VII, VIIIa-VIIIg, or IXa-IXg.

A further aspect of the invention provides a method for treating a L-cystine crystal related condition in a human or animal comprising administering to a human or animal a pharmaceutically effective amount of a compound according to formula I, II, III, IVa-IVc, Va-Vd, VIa-VIg, VII, VIIIa-VIIIg, or IXa-IXg.

A further aspect of the invention provides a combination to treat or prevent an L-cystine crystal-related condition consisting of a compound according to formula I I, II, III, IVa-IVc, Va-Vd, VIa-VIg, VII, VIIIa-VIIIg, or IXa-IXg, and another treatment or treatments, which may include high fluid intake or alkalinizing potassium or sodium salts.

In one embodiment, with respect to the above methods, the L-cystine related condition is cystinuria.

In one embodiment, with respect to the above methods, the L-cystine related condition is kidney stone disease.

In certain aspects, the present invention provides prodrugs and derivatives of the compounds of the invention. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

The present invention also relates to the pharmaceutically acceptable acid addition and base salts of any of the aforementioned compounds of invention. The acids which are used to prepare the pharmaceutically acceptable acid addition salts of the aforementioned base compounds of this invention are those which form non-toxic acid addition salts, ie., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful according to the invention that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful according to the invention that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description, examples, and the claims.

Pharmaceutical Applications

For pharmaceutical uses, it is preferred that the compounds of the invention are part of a pharmaceutical composition. Pharmaceutical compositions, comprising an effective amount of such a compound in a pharmaceutically acceptable carrier, can be administered to a patient, person, or animal having a disease, disorder, or condition as described herein.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions of the invention can be adapted for oral, and parenteral administration, and can be in unit dosage form, in a manner well known to those skilled in the pharmaceutical art. Parenteral administration includes but is not limited to, injection subcutaneously, intravenously, intraperitoneally or intramuscularly. Oral application is preferred, however.

For oral administration, gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5-15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

As will be understood by those in the art, the compositions and pharmaceutical compositions of the invention may be provided in the form of a kit. Kits of the invention comprise one or more specific compositions and/or pharmaceutical compositions of the invention. Optionally, the kit further contains printed instructions as a label or package insert directing the use of such reagents to modify skin pigmentation, i.e., to lighten skin as appropriate to the particular included composition. These compounds are provided in a container designed to prevent contamination, minimize evaporation or drying of the composition, etc. The compounds may or may not be provided in a preset unit dose or usage amount.

General Methods of Preparation

The compounds of this invention can be purchased from commercial sources and tested for their activities. The test compounds which are not commercially available can be prepared from readily available starting materials using various general methods and procedures known in the art. For example, the compounds may be synthetically prepared from known starting materials by conventional laboratory procedures and protocols. Likewise, those compounds that may be found in existing natural materials may be isolated and/or purified by known procedures, to attain the requisite concentration and content of the active, to be efficacious when formulated into compositions in accordance with the present invention. Such preparations may also be described as formulations or materials that are enriched for the particular compound(s) of the invention, and the present invention embraces such preparations within its scope.

Additionally, as will be apparent to those skilled in the art with respect to the methods of preparation of the compounds of the invention involving organic synthesis, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

Materials:

L-cystine (99%), cystamine dihydrochloride (98%), L-cystine dimethylester dihydrochloride (≧95%), poly (acrylic acid) partial sodium salt (50 wt % in $H_2O$, 5 kDa), poly-L-aspartic acid sodium salt (12.3 kDa), poly-L-glutamic acid sodium salt (13.6 kDa), poly-L-lysine hydrobromide (15 kDa), poly-L-arginine hydrochloride (14 kDa), apo-transferrin (human, >98%), chondroitin (sulfate A sodium salt from bovine trachea), human serum albumin (fatty-acid free, 99%), sodium citrate (dihydrate), S-tert-butylmercapto-L-cysteine, D-penicillamine disulfide, and 3,3'-dithiodipropionic acid (99%), L-cysteine (>97%), and L-cysteine methyl ester hydrochloride (98%) were received from Sigma Aldrich and used without purification. Osteopontin, extracted and purified from bovine milk, was donated by Esben Sorenson (University of Aarhus, Denmark) and contains 7 wt % $Ca^{2+}$ ions (as determined with ion chromatography). Tamm-Horsfall protein (THP) was obtained from a human sample with no personal or family history of kidney stone disease. THP was isolated and purified using previously reported procedures, and a portion of the native protein was desialylated by treatment with the enzyme neuraminidase (resulting in a 50% reduction of carbohydrate content). Type I and type III antifreeze proteins (AFPs) purified from cold ocean teleost fish were used as received from A/F Protein, Inc. (Waltham, Mass.). All solutions were prepared using deionized water (18.2 MΩ) purified with a Direct-Q 3 Millipore purification system.

Synthesis of Compound of the Invention

Compound 1

Synthesis and Characterization of L-Cystine Methyl Ester (CME)

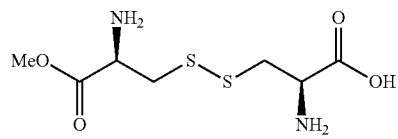

L-cystine methyl ester (CME)

Synthetic Scheme:

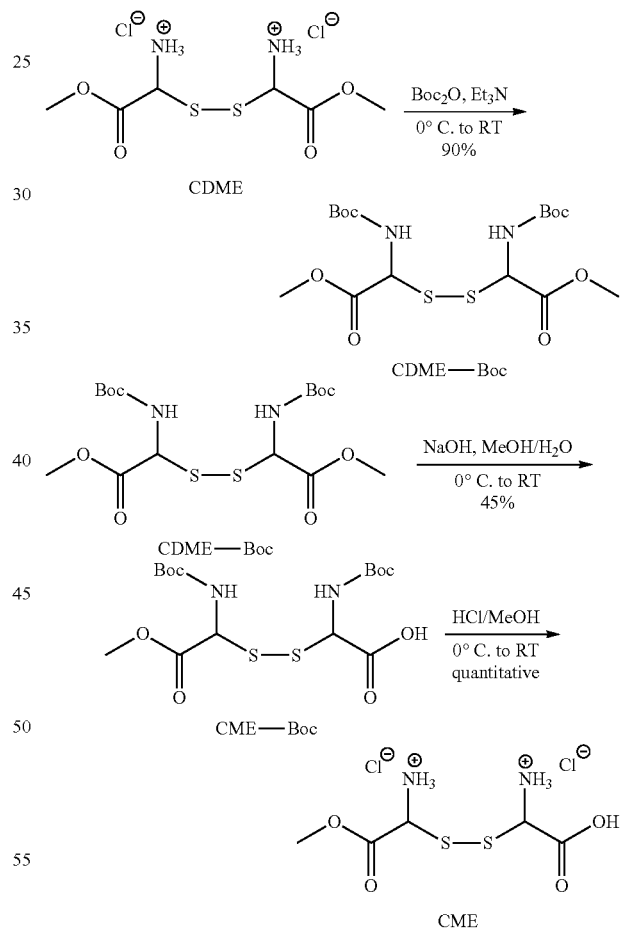

Synthesis of CDME-Boc $Et_3N$ (2.6 g, 17.6 mmol) was slowly added to a stirred solution of CDME (1.5 g, 4.4 mmol, Compound 2) in $CH_2Cl_2$ (20 mL) at 0° C. After stirring for 10 min, di-tert-butyl dicarbonate (T-Boc, 2.2 g, 10.12 mmol) in $CH_2Cl_2$ (20 mL) was added dropwise over the course of approximately 2 hours. The reaction was stirred overnight and allowed to slowly warm to room temperature. The mixture was extracted with CH$_2$Cl$_2$ (2×200 mL). The combined organic layers were dried over Na$_2$SO$_4$ and concentrated in vacuo. The residue was purified by column chromatography on silica gel (hexane/ AcOEt=11/7) to yield the compound CDME-Boc. $^1$HNMR (400 MHz, CDCl$_3$): δ=5.4 (br, 2H), 4.6 (br, 2H), 3.8 (s, 6H) 1.45 (s, 18H). $^1$HNMR spectra of CDME-Boc exhibit a ratio of 3:1 for the H peak of Boc to methyl ester.

Reduction of CDME-Boc to CME-Boc

To a stirred solution of CDME-Boc (0.5 g, 1.1 mmol) in methanol (20 mL) was slowly added NaOH (0.054 g, 1.3 mmol) in water (20 mL) for approximately 2 hours at 0° C. After stirring the solution overnight and allowed it to reach room temperature, 0.5 M HCl was added to achieve a pH 1.0 solution. The mixture was extracted with CH$_2$Cl$_2$ (2×200 mL). The combined organic layers were dried over Na$_2$SO$_4$ and concentrated in vacuo. The residue was purified by column chromatography on silica gel (MeOH/CH$_2$Cl$_2$=1/10) to yield CME-Boc. $^1$HNMR (400 MHz, CDCl$_3$): δ=5.8 (br, 2H), 4.5 (br, 2H), 3.8 (s, 3H) 1.45 (s, 18H). $^1$HNMR spectra of the CME-Boc exhibit a ratio of 6:1 for the H peak of Boc to methyl ester.

Removal of Boc from CME-Boc

HCl (37%, 5 mL) was slowly added to a stirred solution of CME-Boc in methanol at 0° C. The reaction mixture was stirred at room temperature for 12 hours. The solvent was evaporated and the final product (CME) was dissolved in water. CME was obtained after lyophilization. $^1$HNMR (400 MHz, CDCl$_3$): δ=4.5 (br, 1H), 3.8 (s, 3H). $^1$HNMR spectra of the CDME-Boc exhibit a ratio of 3:1 for the H peak of Boc to methyl ester.

CDME Ester Reduction

A solution of molar composition 1 CDME: 1 NaOH: 4204 H$_2$O: 8869 p-dioxane was refluxed for 12 hrs followed by continuous stirring for 12 hrs at room temperature, then removal of solvent by rotary evaporation. The $^1$H NMR spectra of the product in D$_2$O was estimated to contain a molar composition of 1.95 CME: 1.0 CDME: 0.9 L-cystine, with 50.1% conversion of CDME to CME. It should be noted that the reduction reaction requires reflux, while experiments without reflux (i.e. stirring for 24 hrs at room temperature) resulted in no observable conversion of CDME to CME, as confirmed from analysis of product(s) by LC-MSD (in methanol) for a synthesis with 11:1 molar ratio of CDME: NaOH.

Alternate Synthesis of CME and CDME

The compounds cystine dimethyl ester and cystine monomethyl ester may be prepared according to the procedures described in WO 2006102722. The procedures are reproduced below.

Compound 2

Synthesis of Cystine Dimethyl Ester Dihydrochloride (CDME)

A stream of dry hydrogen chloride gas was sparged rapidly into a suspension of cystine (10 g) in anhydrous methanol (50 mL) and agitated with a magnetic stirrer. After all the cystine had dissolved the warm solution was cooled in an ice bath, and sparging of HCl continued to saturation at 0-5° C. The reaction mixture was protected from atmospheric moisture with a calcium chloride drying tube and allowed to stand at room temperature for 3 hours. Solvent was removed from the reaction mixture under reduced pressure on a o rotary evaporator with the water bath set at 50° C. An aliquot of methanol (50 mL) was added to the resulting syrup and then concentration by rotary evaporation repeated. To the dry syrupy residue was added anhydrous ether (20 mL) resulting in spontaneous crystallization. The mixture was allowed to stand overnight at 4° C. and the resulting crystalline suspension was collected by filtration in a buchner funnel and washed with cold anhydrous ether (30 mL). The filter cake was dried under reduced pressure over potassium hydroxide pellets in a desiccator.

For the synthesis of cystine dimethyl ester, the following procedure may be used, optionally scaled up. A suspension of cystine (20 g) in methanol (300 mL) under reflux is constantly bubbled through with dry hydrogen chloride gas for 2 hours. After an additional hour at room temperature the reaction mixture is concentrated on a rotary evaporator under reduced pressure, methanol (50 mL) is added and the evaporation to dryness repeated. The dry residue is diluted with ether (50 mL), allowed to stand overnight at 4° C., resulting in a crystalline suspension which can be collected by filtration in a buchner funnel, followed by washing with ether. The filter cake is then dried under reduced pressure over silica and sodium hydroxide pellets in a desiccator.

Synthesis of the monomethyl ester of cystine may be performed by a similar route by using only half the molar equivalent of methanol, saturating the cystine/methanol in a chloroform solution with hydrogen chloride gas and heating to a gentle reflux for 1 hour and then cooling to room temperature for approximately 1 hour. The reaction product is worked up as described in the above example.

Another Alternate Method to Prepare CDME

The ester may be prepared by the procedure described in Tetrahedron: Asymmetry, 12(11), 1615-1620; 2001.

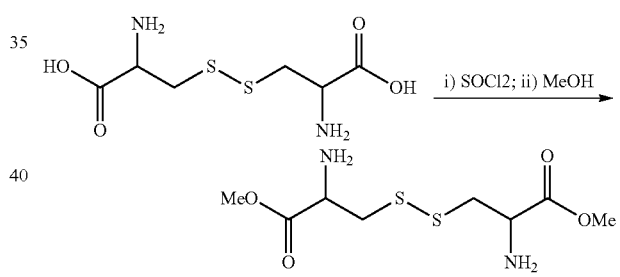

Yet Another Alternate Method to Prepare CDME

The ester may be prepared by the procedure described in Journal of Organic Chemistry, 60(11), 3266-7; 1995:

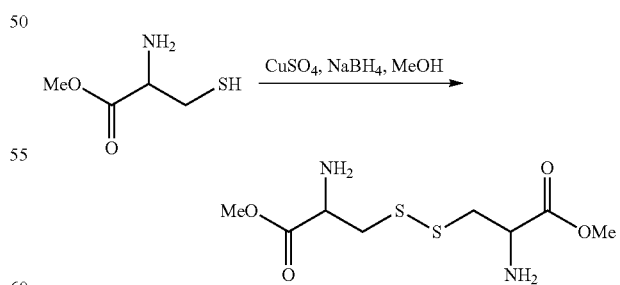

Synthesis of Cystine Diethyl Ester

The cystine diethyl ester may be prepared by following the synthetic method described in Journal of the American Chemical Society, 119(39), 9309-9310; 1997.

Compound 3

Synthesis of Cystine Diethyl Ester

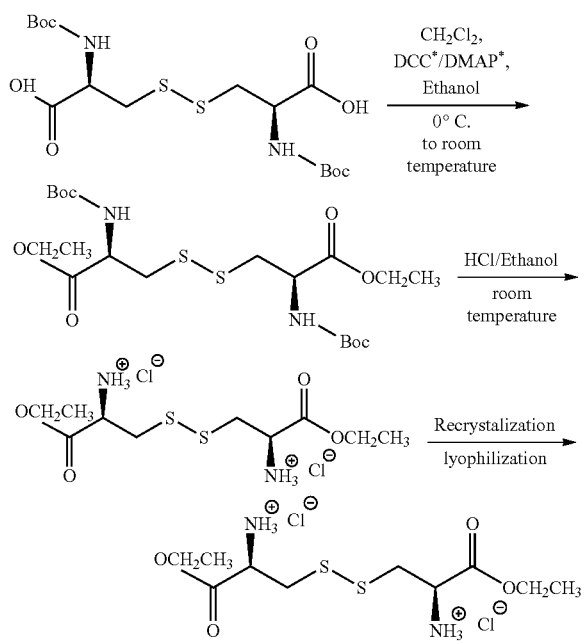

*DCC: N,N'-Dicyclohexylcarbodiimide DMAP: 4-(Dimethylamino)pyridine

Step 1: Synthesis of L-CDEE-Boc

CH$_2$Cl$_2$ (20 mL) and ethanol (1.5 mL) were added to the L-cys-Boc (2.0 g) and DMAP (0.1 g). After stirring for 10 min, DCC (2.8 g) was added into the solution over 30 min. The reaction was stirred overnight and allowed to warm slowly to room temperature. The solution was filtered and the solvent removed by vacuum evaporation. The residue was purified by column chromatography on silica gel (hexane/EtOAc=7/3) to yield L-CDEE-Boc.

$^1$HNMR (400 MHz, CDCl$_3$): δ=5.39 (br, 1H), 4.46 (br, 1H), 4.05 (br, 2H), 1.45 (s, 9H), 1.20 (br, 3H). $^1$HNMR spectra were recorded using a Bruker AVANCE 400 spectrometer using broadband decoupling.

Step 2: Removal of Boc from L-CDEE-Boc 70 ml 1.25M HCl/Ethanol was added to L-CDEE-Boc (1.5 g) and stirred overnight. The mixture was extracted with H$_2$O (2×200 mL) and L-CDEE was obtained as the hydrochloride salt after lyophilization. Pure L-CDEE was obtained by recrystallization from ethanol/ethyl acetate solution.

$^1$HNMR (400 MHz, D$_2$O): δ=4.38 (br, 2H), 4.23 (br, 2H), 3.33 (br, 2H), 1.272 (s, 6H).

Compound 4

Synthesis of L-Cystine Di-Isopropyl Ester (L-CDIE)

The diisopropyl ester is prepared following the procedure described for the Compound 3. Thus, L-cystine-Boc is reacted with isopropanol followed by the deprotection gave the desired diisopropyl ester.

L-CDIE-Boc: $^1$HNMR (400 MHz, CDCl$_3$): δ=5.42 (br, 1H), 5.07 (br, 1H), 4.56 (br, 1H), 3.17 (br, 2H), 1.45 (s, 9H), 1.16 (br, 6H).

L-CDIE salt: $^1$HNMR (400 MHz, D$_2$O): δ=5.08 (br, 1H), 4.45 (br, 1H), 3.30 (br, 2H), 1.250 (s, 6H).

Compound 5

Synthesis of Cystine Di-T-Butyl Ester

Cystine di-t-butyl ester or other alkyl esters may be prepared by following synthetic methods described in Angewandte Chemie, International Edition, 47(49), 9472-9475; 2008; and in Journal of Organic Chemistry, 68(21), 8185-8192; 2003.

Alternately, the di-t-butyl ester was prepared following the procedure described below.

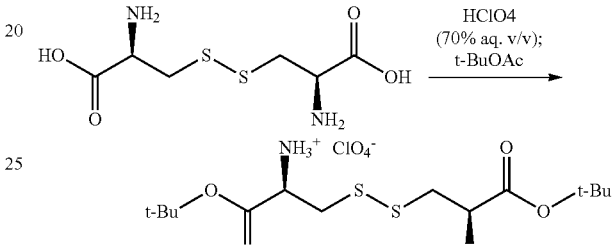

L-cystine (10.0 g, 42 mmol) was dissolved in perchloric acid (70% aq. v/v, 16.6 mL) followed by slow addition of 100 mL tert-butyl acetate. After stirring the mixture overnight, a white solid formed. The mixture was chilled in ice for 30 min, filtered, and washed with cold ethyl ether several times to yield L-CDTE perchlorate. L-CDTE perchlorate: (400 MHz, MeOD$_4$): δ=4.35 (br, 1H), 3.40 (m, 1H), 3.25 (m, 2H), 1.56 (s, 9H).

Synthetic Methods to Prepare Cystine Sulfoxides and Sulfone Derivatives

The cystine sulfoxides and sulfone derivatives may be prepared by following synthetic methods described in Tetrahedron Letters, 45(50), 9237-9240; 2004; or in Journal of Organic Chemistry, 50(22), 4332-6; 1985.

Additional General methods for sulfoxides and sulfones may be found in Tetrahedron Letters (2004), 45(50), 9237-9240.

General Synthetic Methods to Prepare N-Alkyl Cystine s Derivatives

The N-alkyl derivatives may be prepared by following synthetic methods described in Indian Journal of Chemistry, Section B: Organic Chemistry Including Medicinal Chemistry, 37B(1), 10-14; 1998; Heterocycles, 67(2), 519-522; 2006; or in Indian Journal of Chemistry, Section B: Organic Chemistry Including Medicinal Chemistry, 37B(1), 10-14; 1998.

Additional methods to prepared compounds of the invention may be found in:

Facile Synthesis of β-Amino Disulfides, Cystines, and their Direct Incorporation into Peptides.

Nasir, Baig R. B.; Kanimozhi, Catherine K.; Sudhir, V. Sai; Chandrasekaran, Srinivasan. Department of Organic Chemistry, Indian Institute of Science, Bangalore, India. Synlett (2009), (8), 1227-1232; and Conversion of Thiosulfinate Derivatives of Cystine to Unsymmetrical Cystines and Lanthionines by Reaction with tris(dialkylamino)phosphines.

Olsen, Richard K.; Kini, Ganesh D.; Hennen, William J. Dep. Chem. Biochem., Utah State Univ., Logan, Utah, USA. Journal of Organic Chemistry (1985), 50(22), 4332-6.

Crystallization of L-Cystine

Preparation of Hexagonal L-Cystine Crystals:

Syntheses of L-cystine reported in the literature vary in approach, often employing acidic solutions (pH<1) that generate three crystalline structures: L-cystine dihydrochloride, L-cystine dihydrochloride dihydrate, and L-cystine (hexagonal). A reported protocol for recrystallization of L-cystine in 0.5% HCl was followed [S1], which yielded largest crystals with (0001) surfaces void of observable steps, as confirmed by AFM topographical imaging that revealed roughened surfaces without terraces. This protocol was modified by using solutions at physiological pH (i.e. pH ~7), which generated hexagonal crystals with multiple, terraced steps that were visible even by optical microscopy. Hexagonal L-cystine crystal platelets were synthesized for AFM measurements of surface topography and real time in situ growth. A supersaturated L-cystine solution was prepared by adding 70 mg of L-cystine to a 250 mL round-bottom flask containing 100 mL of deionized water. A heating mantle was pre-heated for 10 min, and then the supersaturated L-cystine solution was refluxed at 100° C. for 20 min with stirring to completely dissolve L-cystine. The boiling solution was gradually cooled on the heating mantel while continuously condensing and stirring for 75 min. The solution was then transferred into a 100 mL beaker, sealed to prevent evaporation and exposure to airborne particulates, and stored overnight at room temperature without stirring. Single crystals were collected by vacuum filtration (Whatman Grade 1 filters, >11 μm pores) and were air dried prior to analysis.

Alternately, the hexagonal crystals can be obtained by crystallization performed near neutral pH (Sα) The hexagonal form was crystallized from a supersaturated L-cystine solution prepared by adding 70 mg of L-cystine to 100 mL of deionized water (3 mM), and heating under reflux at 100° C. for 20 min with stirring to completely dissolve L-cystine. The resulting solution corresponds to a relative supersaturation of σ~7.5, based on the lower bound of reported solubility (0.4-0.7 mM at pH 7, 25° C.) (Sb,Sc,Sd). This concentration was used for bulk crystallization studies in the presence of additives, so that a measurable amount of bulk crystals could be obtained in a reasonable time. The solution was then allowed to cool slowly with stirring for 75 min. 30 mL aliquots were transferred to separate glass containers, which were then sealed to prevent evaporation and exposure to airborne particulates and stored for 72 hours at room temperature without stirring. Single crystals were collected by vacuum filtration (Whatman Grade 1 filters, >11 μm pores) and were air dried prior to analysis. The crystals retrieved in this manner were used for AFM studies by mounting individual crystals according to the procedure described below.

Bulk Crystallization in the Presence of Additives.

Various proteins, poly-amino acids, and molecular mimics of L-cystine were examined as additives. The aforementioned procedure for hexagonal platelet crystallization was repeated. Following the 75 min cooling period, prior to any observable crystallization, the additive was added to the supersaturated L-cystine solution to the desired concentration. The container was sealed and stored for 72 hours at room temperature without stirring, after which the precipitate was collected by vacuum filtration (Whatman Grade 1 filters, >11 μm pores) and were air dried prior to analysis. Crystallization without additive was performed in an identical manner for comparison using a control solution from the same batch. The mass yields of L-cystine crystals were obtained by dividing the mass of L-cystine crystals (collected from growth solution by filtration) by the mass of L-cystine added in the growth solution. The crystals were isolated with 11 μm-pore filters, which were regarded as sufficiently small for reliable capture of the crystals (optical micrographs reveal that the size of crystals was always greater than 50 μm

Materials Characterization

An Orion 3 Star pH meter (Thermo Electron Corp.) with Orion 9157BNMD probe was used to measure the pH of L-cystine solutions. Crystal morphology was measured with a Leitz ERGOLUZ optical microscope and a Hitachi 3500 scanning electron microscopy. A thin coating of gold (2 nm) was sputtered on SEM samples and images were acquired at low voltage (2-5 kV) to minimize sample melting. $^1$H NMR spectra were recorded using a Bruker AVANCE 400 spectrometer and were routinely run using broadband decoupling. Chemical shifts (δ), expressed in ppm, are referenced to the corresponding residual nuclei in deuterated solvent ($D_2O$). Powder X-ray diffraction (XRD) patterns of isolated crystals were acquired with a Panalytical XPert PRO MPD using a Bragg-Brentano geometry with fixed slits at power settings of 45 kV and 40 mA. A CuKα radiation (0.154 nm) source was used with a 1 degree fixed divergence slit (10 mm beam mask) for incident X-rays and a 1 degree anti-scatter slit Ni filter (1/16 degree receiving slit) for diffracted X-rays.

Single Crystal X-Ray Diffraction (SCXRD):

Patterns were acquired with a Bruker SMART ApexII CCD area detector on a D8 goniometer. The temperature during the data collection was controlled with an Oxford Cryosystems Series 700 plus instrument. Preliminary lattice parameters and orientation matrices were obtained from three sets of frames. Data were collected using graphite-monochromated and 0.5 mm-MonoCap-collimated Mo—$K_\alpha$ radiation (λ=0.71073 Å) with the ω scan method (Bruker APEXII). Data were processed with the SAINT+ program for reduction and cell refinement. Multi-scan absorption corrections were applied by using the SADABS program for area detector. The structure was solved by the direct method (SHELXS-97) and refined on $F^2$ (SHELXL-97) (G. M. Sheldrick, Universität Göttingen, Germany).

AFM Characterization:

A Digital Instruments (Santa Barbara, Calif.) Nanoscope IIIa Multimode system was used for topographical and lattice imaging. All measurements were performed in contact mode using Veeco NP-B $Si_3N_4$ cantilever tips with a spring constant of 0.12N/m (triangular, 196 μm length, 41 μm width) on a glass cantilever holder, and a liquid cell was created for in situ step velocity measurements. All L-cystine crystals for AFM measurements were prepared by method 1. Crystals were transferred onto an AFM specimen disk coated with partially cured (1 hr) UV-curable optical cement (Type SK-9, EMS Acquisition Corp.) by gently pressing the disk against hexagonal platelets or L-cystine needles isolated by filtration (Whatman Nuclepore membrane, 8 μm). The (0001) face of hexagonal platelets was exposed normal to the disk for AFM analysis with growth occurring along equivalent {1010} faces in the lateral directions, while the sides of L-cystine needles were exposed normal to the disc. The partially cured polymer with adhered crystals was completely cured by additional UV radiation (2 hrs) prior to analysis. Measurements of individual step heights for hexagonal L-cystine crystals were acquired in air (contact mode) at a scan rate of 1.00 Hz and 256 samples per line over a 15×15 μm$^2$ surface area. Integral and proportional gains were set to the highest possible values without obtaining feedback. Four hexagonal crystals (5 areas per crystal) were analyzed for statistical step height distributions, which were calculated from >$10^3$ individual steps. Lattice-resolved images of crystal surfaces were acquired in water (contact mode) using a scan rate of 112 Hz over a 12×12 nm$^2$ area.

Alternate Protocol for AFM Measurements

Atomic force microscopy was performed with a Digital Instruments (Santa Barbara, Calif.) Nanoscope IIIa Multimode system. All measurements were performed in a cell designed to contain liquids for in situ imaging, including step velocity measurements. All measurements were performed in contact mode using Veeco NP-B $Si_3N_4$ tips on silicon nitride cantilevers with a spring constant of 0.12N/m (triangular, 196 μm length, 41 μm width). L-cystine crystals (hexagonal form) were transferred onto an AFM specimen disk coated with partially cured (1 hr) UV-curable optical cement (Type SK-9, EMS Acquisition Corp.) by gently pressing the disk against hexagonal platelets collected by filtration (Whatman Nuclepore membrane, 8 μm). The (001) faces of the hexagonal plates naturally aligned parallel with the specimen disk such that the velocity of the equivalent {100} steps could be measured readily by AFM, The partially cured polymer with the adhered crystals was cured completely by additional UV radiation (2 hrs) prior to analysis. The mounted L-cystine crystals were etched slightly by immersion in deionized water for 30 sec at 60° C. to remove amorphous deposits or impurities that may be present on the surface. Step velocities on the hexagonal L-cystine crystals were measured by AFM using a fluid cell containing an aqueous solution, supersaturated with L-cystine (2 mM), introduced to the cell via a syringe. Step velocities were determined by measuring the distance of the steps from a reference point, usually the dislocation core, in consecutive deflection images acquired at periodic intervals, ranging from 9-14 sec. Measurements were acquired under continuous flow of fresh solution in order to maintain constant supersaturation and additive concentration. The step advancement under flow revealed a linear dependence of the step position on time, which was used to determine the step velocities. The step velocities, which correspond to the crystal growth rates, were measured with and without inhibitor for each pair.

Crystallization in Presence of CDME

Figure 3:
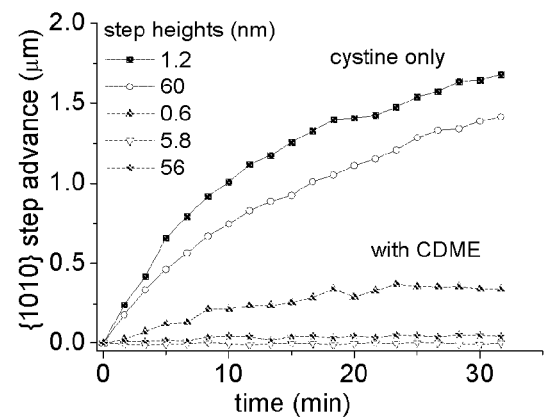
FIG. 3 depicts the rate of growth, as measured by atomic force microscopy, of L-cystine crystals in the absence and presence of the growth inhibitor CDME.
(A) Step advancement on the (0001) surface of L-cystine as measured by AFM for various step heights in L-cystine solutions (0.5 g/L) without additives (blue) and with 5.0 g/L CDME (red). The advancement of 0.6 nm-high steps, equivalent to c/6 and therefore corresponding to terrace L-cystine molecules, is attenuated by CDME. The growth of steps with heights >0.6 nm is completely suppressed. Growth was monitored under static conditions (i.e. no continuous flow); step advancement is rapid initially, slowing somewhat to a constant rate due to a reduction in L-cystine concentration from adventitious crystallization outside the field of view.

AFM measurements reveal that CDME, a structural mimic of L-cystine with carboxylate groups replaced by methyl ester groups, has a pronounced effect on L-cystine growth. AFM growth studies, which employ a large excess of CDME to quantify growth inhibition at a reasonable timeframe, reveal that CDME suppresses the advancement of {1010} steps with heights larger than 1 nm (FIG. 3), which corresponds to two or more L-cystine molecules along the c-axis. The advancement of 1-nm steps, equal to a layer of a single L-cystine molecule, is inhibited by CDME, which reduces the step velocity from 29 nm/min in the absence of additive to 7 nm/min in the presence of additive, but does not completely suppress growth. This suggests that CDME binding to ledge sites (i.e. intersection of {1010} and (0001) planes) is obstructed by steric interactions between the CDME methyl ester groups and L-cystine amine groups, which is consistent with the experimental observation that CDME does not suppress 1-nm step advancement.

CDME binds to {1010} faces through interactions of amine groups and sulfur atoms of CDME with carboxylate groups and sulfur atoms of L-cystine, respectively. CDME methyl ester groups serve as perturber moieties, which inhibit the attachment of L-cystine amine groups to bound CDME and frustrate L-cystine adsorption at sites adjacent to bound CDME. This mechanism is illustrated in FIG. 3B, where the binding of a single CDME molecule to {1010} steps blocks three crystal sites for L-cystine attachment. Ledge sites are unfavorable for CDME binding, while non-ledge sites are as equally accessible for CDME binding. It is likely that L-cystine molecules in the c-axis are not equally accessible for CDME binding, namely sites where the amine groups of L-cystine are oriented normal to the {1010} crystal face which may inhibit CDME binding via steric interactions with CDME methyl ester groups.

Figure 9:
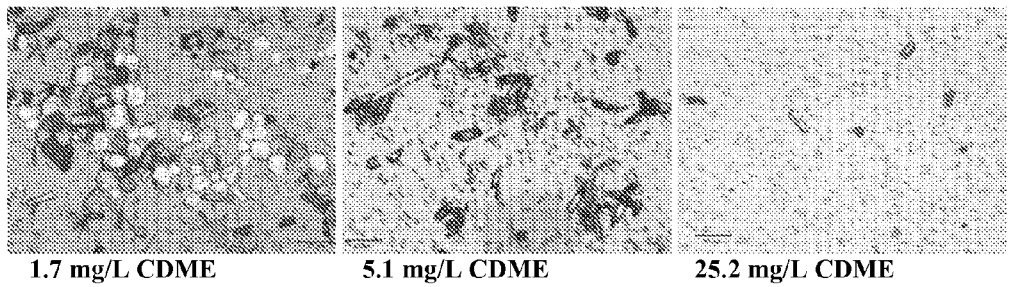
FIG. 9 depicts optical micrographs of L-cystine crystals grown in the presence of various concentrations of CDME. Optical micrographs of L-cystine crystals isolated by filtration (8 μm pore) from bulk crystallization in supersaturated L-cystine solutions (700 mg/L) containing increasing concentrations of CDME (1.7 to 25.2 mg/L). Growth without additive results in the formation of large hexagonal platelets (average size of 200-400 μm). In the presence of low CDME concentrations (1.7 mg/L), the size of hexagonal platelets is dramatically reduced (50-100 μm) and a population of hexagonal needles are observed. As the concentration of CDME is further increased (5.1 mg/L), the predominant morphology is needles. In most syntheses there are a mixture of hexagonal platelets, hexagonal needles, and needles of an unknown crystalline structure. Increases in CDME concentration (25.2 mg/L) reduces both the needle size and the number of needles collected by filtration. Note: scale bars=100 μm.

Growth inhibition is facilitated at the molecular level by CDME binding to {1010} surfaces, which shifts the fastest growth along the [001] direction (FIG. 3C). On a macroscopic level, CDME alters the L-cystine crystal habit from hexagonal platelets to hexagonal needles (FIG. 2C) with six equivalent {1010} surfaces. The transition from platelets to needles shifts the largest surface area from the {0001} face to the {1010} face and reduces crystal surface area by nearly two orders of magnitude. As the CDME concentration is increased from 0 to 5 mg/L, hexagonal platelets decrease in size in favor of a polydisperse distribution of needles (FIG. 9). The (0001) face of hexagonal platelets crystallized in the presence of CDME is largely comprised of 1-nm steps (FIG. 10), but as the concentration of CDME approaches 5 mg/L platelet formation is suppressed and the mass yield of needles is more than 70% less than the yield of platelets in the absence of additive (Table 1). As the CDME concentration is increased further to 25 mg/L (3 wt %), the number of needles is negligible (FIG. 9).

Figure 4:
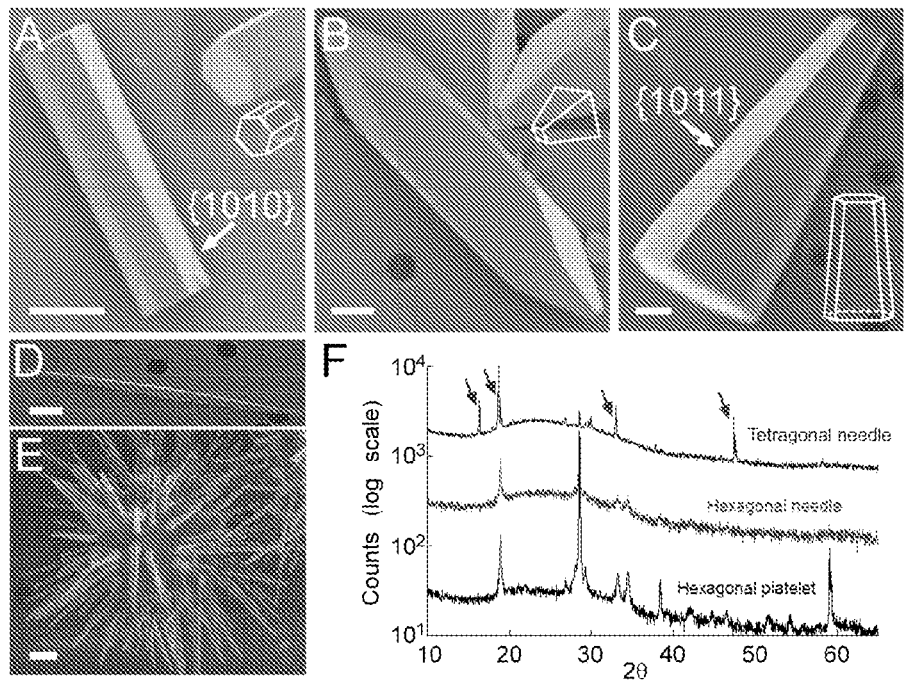
FIG. 4 depicts cystine crystals grown in the presence of growth inhibitors CDME and CME, along with powder X-ray diffraction patterns verifying the crystal phases.
CDME and CME tailored growth of L-cystine crystals (scale bars=10 μm). L-cystine crystallization in 5 mg/L additive solutions generates hexagonal needles with aspect ratios (LW=length-to-width) that vary between LW=1-30. (B) Crystallization in CDME solutions generates tetragonal needles with ellipsoid and irregular pentagon facets. (C) Crystallization in the presence of CME produces tapered, hexagonal needles with {1011} faces and aspect ratios that vary between (C) LW=20 and (D) LW=2. (E) L-cystine crystallization in CME solutions generates sea urchin-like architectures with hundreds of needles that radially protrude from an apparent amorphous inner core. (F) XRD patterns of tetragonal and hexagonal needles compared to hexagonal platelets crystallized in the absence of additive. Bulk crystallization of L-cystine with CDME yields either hexagonal needles or a mixture of hexagonal needles with a much larger population of tetragonal needles (peaks indicated by arrows).
Figure 5:
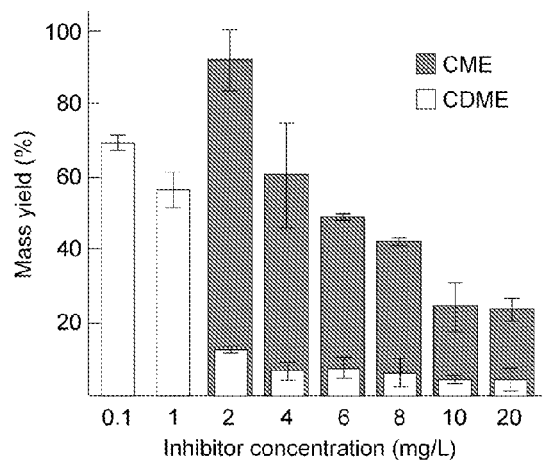
FIG. 5 depicts the histogram of mass yields of L-cystine crystals grown in the presence of CDME and CME.
The total mass of L-cystine crystals obtained after crystallization for 72 hours in the presence of various concentrations of CDME and CME. The error bars represent one standard deviation, based on multiple trials.
Figure 6:
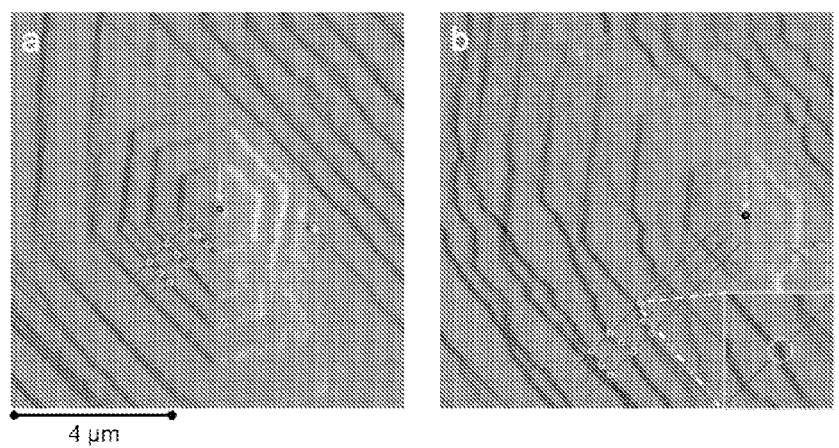
FIG. 6 depicts atomic force microscopy images of L-cystine crystal surface acquired in deflection mode.
AFM deflection images illustrating the method used for step velocity measurements. (a) AFM deflection image for the (0001) surface at the initial time of the growth experiment. A straight line (blue dotted line) was drawn for each step to define structurally equivalent {1010} faces of the hexagonal crystal, and three lines perpendicular to the step plane (red solid lines) were drawn to indicate the direction of growth. Yellow circles at the cross points of the red and the blue lines indicate step positions with respect to a reference point, represented as a black circle pointed by a yellow arrow. The same procedure was followed for each deflection image, and the growth rates were obtained by monitoring the advancement of the yellow circles (i.e. the cross points of the red lines and the {1010} faces). Measuring the growth rates with respect to the reference point ensured the accuracy of the step velocities regardless of frame shifts, which often occurred in an unpredictable manner during the experiment. Usually a pit on the crystal surface that remained intact throughout the growth measurement served as a reference point, but in this example a nucleation center was used instead. The growth rate of a single step was measured three times (i.e. 3 red lines per step), and the average value was taken as its step velocity. (b) AFM deflection image obtained after 17 min of growth. A change in the position of the reference point indicates a shift in the scan area due to instrument drift. The {1010} faces do not always grow in a linear fashion, meaning that some steps do not maintain a straight-edge as they advance. When one section of a step advances faster (i.e. three cross points of a single step did not move at the same rate), it was difficult to assign {1010} faces with a straight blue line, thus cross points between individual steps and redlines were measured as shown in the inset.

A shift in crystal morphology from hexagonal platelets to hexagonal needles supports a mechanism for CDME binding to {1010} faces. Interestingly, CDME growth inhibition also yields needles with a tetragonal crystal structure. L-cystine crystallization in CDME yields a mixture of tetragonal and hexagonal crystal structures, as evidenced by the X-ray diffraction (XRD) patterns of tetragonal and hexagonal needles from CDME solutions compared to hexagonal platelets crystallized in the absence of additive (FIG. 4F). Tetragonal needles are more abundant in bulk crystallization batches than hexagonal needles, which is opposite reports of L-cystine crystallizations in basic solutions where tetragonal crystals are generated in trace quantity relative to hexagonal platelets [10].

Figure 10:
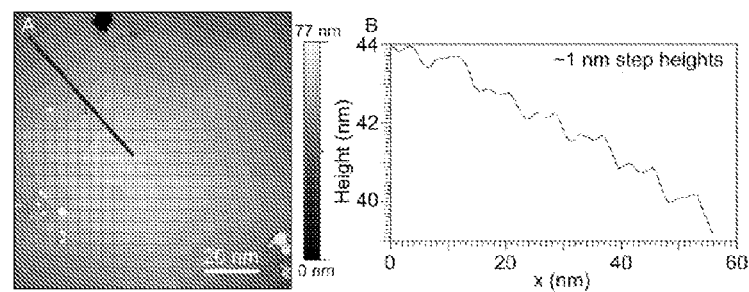
FIG. 10 depicts AFM topographical images of hexagonal L-cystine acquired in the presence of CDME, illustrating the prevalence of 1 nm high steps.
(A) An AFM topographical image of hexagonal L-cystine crystallized in a supersaturated L-cystine solution with 1.7 mg/L CDME reveals multiple steps grown from the screw dislocation at the center of the image. (B) A step height profile of the AFM image (blue line in (A)) reveals that step heights on the (0001) surface are approximately equal to 0.9 nm, which is the length of a single L-cystine molecule.

L-cystine crystallizes into hexagonal platelets (50-400 μm) in the absence of growth inhibitors. The morphology of hexagonal crystals is typically non-symmetric due to twinning and defects, which generate a distribution of crystal sizes and shapes. Crystal aggregates observed in optical micrographs may be attributed, in part, to the isolation procedure that involves both filtering and drying of crystals. In the presence of CDME, L-cystine crystal morphology dramatically changes from hexagonal platelets to needles with individual volumes that are two orders of magnitude smaller than the hexagonal platelets. Crystallization in CDME solutions yields a distribution of particles, which include hexagonal platelets, square needles, and hexagonal needles. As the CDME concentration is increased from 0 to 2 mg/L, there is a decrease in hexagonal platelet size with and the number of platelets decrease in favor of needles (FIG. 9). AFM topographical images of a hexagonal platelet crystallized in the presence of CDME reveal steps on the (0001) surface with sizes nearly 1-nm in height (FIG. 10). At 5 mg/L CDME, platelet formation is suppressed and further increase in CDME concentration reduces the number of needles. Trace number of needles were observed after filtering crystals (8 μm filter pores) from supersaturated L-cystine solutions containing 25 mg/L CDME (FIG. 9), suggesting 3 wt % CDME is sufficient to suppress crystallization.

A 5 mg/L CDME concentration in 700 mg/L supersaturated solutions of L-cystine alter crystal morphology from hexagonal platelets in the absence of additive to needles with two distinct morphologies: hexagonal needles and square needles. Needles with square geometries exhibit a distribution of ellipsoidal habits and irregular pentagon habits. Some particles (<10 µm) lack a distinct habit. These particles may be small crystals that have not developed facets or they may be amorphous material.

Crystallization in Presence of CME

To examine further the mechanism of L-cystine growth inhibition, we synthesized L-cystine methyl ester (CME), an unsymmetrical disulfide with one half similar to CDME (methyl ester group) and the other half similar to L-cystine (carboxylate group). CME binds to ledge sites with its carboxylate group, which structurally mimics L-cystine, while the methyl ester group frustrates 1-nm step growth analogous to CDME inhibition of larger steps. The synthesis of CME proved to be challenging, which prevented AFM measurements at the same inhibition concentration (~5 g/L) as CDME. SEM images, however, reveal that CME has a distinct influence on L-cystine crystal size and habit. CME growth inhibition generates tapered hexagonal crystals with six equivalent {1011} surfaces (FIG. 2E) and thin needles observed both as individual crystals (FIG. 4D) and as sea urchin-like architectures (FIG. 2F), which are superstructures of needles that protrude radially from an apparent amorphous core. Bulk crystallization reveals that a CME concentration more than twice that of CDME is needed to achieve similar crystal growth inhibition, which qualitatively agrees with the mechanism wherein a single CME molecule blocks two sites on the crystal surface compared to CDME, which blocks three sites.

Influence of CME on L-Cystine Crystallization

CME syntheses result in a mixture of the initial reagent (CDME), the desired product (CME), and the fully reduced product (L-cystine). Bulk crystallization experiments reveal that CME effects crystal habit, wherein CME binding to crystal surfaces generates hexagonal needles with {1011} faces (FIG. 2E), which exhibit an 84.5 degree angle relative to the (0001) basal surface.

Crystallization in Presence of Other Additives

Additives chosen for these studies were various proteins, poly-amino acids, and molecular mimics of L-cystine (see Table 1). The above procedure for hexagonal platelet crystallization was repeated until completion of the 75 min cooling period, at which point 29.5 g of solution was transferred to a 100 mL beaker containing 0.5 g of separately prepared additive solution to yield net concentrations of 2 mg/L additive and 0.7 g/L L-cystine. Additive solutions were replaced with deionized water of equivalent volume for control measurements. The beaker was sealed and stored for two days at room temperature without stirring, after which single crystals were collected by vacuum filtration (Whatman Grade 1 filters, >11 µm pores) and were air dried prior to analysis.

Thiol Growth Inhibitors

Two thiols were investigated as possible growth inhibitors of L-cystine crystallization. Bulk crystallization studies were performed using 10 mg/L thiol, which is nearly two times more than the amount used for studies with CDME due to the fact that thiols have one less perturbing group than CDME. Crystallization in the presence of L-cysteine, which has a molecular structure equal to one-half of L-cystine, had a pronounced effect on the size of L-cystine platelets (FIG. 13), but it did not influence the yield (Table 1). Crystallization in the presence of L-cysteine methyl ester, which has a molecular structure equal to one-half of CDME, had a pronounced effect on both morphology (FIG. 14) and yield (Table 1). L-cystine crystallization in the presence of L-cysteine methyl ester shifted the crystal habit from hexagonal platelets to needles and reduced the mass yield from 80±8% in the absence of additive to 32% in the presence of additive.

Comparison of CDME with Other Inhibitors

It is interesting to compare the effectiveness of CDME with inhibitors of other kidney stone forming materials. CDME inhibits L-cystine growth at concentrations that are comparable to poly-amino acid concentrations (5 mg/L) used to inhibit COM crystallization [27]. Past studies of COM reveal that monomers of poly-amino acids require concentrations 1000-times larger than polymers to achieve similar inhibitory effects, suggesting CDME and CME molecules are potent growth inhibitors. Macromolecules (e.g. polymers and proteins) with proximal functional groups that mimic COM crystal moieties significantly affect crystallization. Surprisingly, we found that polymers and proteins with proximal carboxylate and amine groups, similar to functional groups in L-cystine, had a negligible influence on L-cystine growth— namely, urinary proteins rich in carboxylate residues, such as osteopontin, human serum albumin, and Tamm-Horsfall protein, and poly-amino acids, such as poly-glutamate and poly-lysine (Table 1).

Advantages of CDME

Collectively, AFM and bulk crystal studies suggest that CDME is a viable therapeutic agent for cystinuria, and offers a different approach for treatment through facile attachment to crystal surfaces in benign, physiologically relevant conditions rather than current approaches that use chemical cleavage or dramatically alter urine volume and alkalinity. Growth inhibition induces a kinetic metastable state that maintains L-cystine concentrations above saturation, which parallels current therapeutic approaches aimed to increase L-cystine supersaturation. Toxicity of growth inhibitors is naturally a concern, as cell culture and in vivo animal studies suggest possible adverse affects of CDME (e.g. alterations in adenosine triphosphate and reactive oxygen species levels and cell viability) [28, 29] for dosages between 100 mg/L and 20 g/L per day [28-30]. Our investigations reveal that much lower concentrations of CDME (~25 mg/L) are sufficient to inhibit in vitro L-cystine crystallization. AFM and bulk crystallization studies, however, were performed with a 2 mM L-cystine concentration, which is much greater than physiological concentrations in urine (~0.4 mM), suggesting dosages less than 4 mg/L CDME (a value significantly less than CBTDs) may be sufficient to inhibit in vivo L-cystine crystallization.

An advantage of tailored growth inhibitors over existing therapies is their potential to inhibit multiple pathways of stone formation, which include growth, aggregation, and retention via crystal and/or aggregate adhesion to epithelial cells. Our findings clearly demonstrate that CDME and CME suppress in vitro crystal growth and reduce crystal size. Moreover, CDME and CME may influence the adhesive properties of L-cystine crystals by altering exposed surface areas, which ultimately affect crystal aggregation and retention. SEM cross-sectional images of stones suggest that the large (0001) faces of hexagonal platelets promote aggregation through crystal-crystal stacking along these surfaces (FIG. 7B). CDME and CME dramatically reduce the (0001) surface area of crystals and produce needles with volumes that are nearly 100-times less than hexagonal platelets, thus reducing the overall surface area for aggregation contacts between crystals. Moreover, the predominant surface area in CME needles is the {1011} face, whereas CDME hexagonal needles have large {1010} surfaces and tetragonal needles have a variety of exposed surfaces. It is reasonable to suggest that in vivo needle-needle and needle-cell interactions would differ from those of hexagonal platelets, although the extent to which these interactions inhibit or promote crystal aggregation and retention is an area of ongoing investigation.

In Situ AFM Growth Measurements:

Real time in situ step velocity measurements of L-cystine growth were assessed along six structurally-equivalent {1010} faces of the hexagonal structure. A liquid cell was created with the glass cantilever tip holder, and working solutions were injected through a 1-mL syringe. Prior to injecting the growth medium (i.e. supersaturated L-cystine solution), crystals were etched with deionized water in the fluid cell for one hour to remove amorphous deposits or impurities that may be present on the surface. Supersaturated solutions (0.5 g/L) were generated by adding L-cystine to deionized water, boiling the solution on a heating mantle for 20 min to completely dissolve the solute, and allowing the solution to cool for 20 min on the heating mantle before transferring the solution (via syringe) to the AFM fluid cell. This method allows the solution to gradually cool to room temperature prior to AFM measurements in an effort to minimize premature nucleation of L-cystine in the growth solution.

The effect of additives on crystal growth rates was investigated. Additives were combined with the supersaturated L-cystine following the 20 min cool down period (as discussed above) to avoid denaturing biological additives at higher temperature. A small volume (0.2 mL) of concentrated additive was mixed with 4.8 mL of L-cystine to generate 0.48 g/L L-cystine solutions with additives of varying concentrations: poly-L-aspartate (5 mg/L), AFPs (50 mg/L), S-tert-butylmercapto-L-cysteine (0.5 g/L), CDME, cystamine, poly-L-lysine, and 3,3'-dithiodipropionic acid (5 g/L). Control measurements without additive were performed in a similar manner, replacing concentrated additive solutions deionized water to maintain a constant L-cystine concentration. Data collection was started immediately after injecting the working solution into the AFM liquid cell. For each measurement, growth was first assessed in the absence of additive, then in the presence of additive on the identical area of the crystal surface to analyze relative changes in step velocity. Measurements were acquired at static conditions without refreshment of growth solution using supersaturated L-cystine solutions six times larger than the solubility of L-cystine in water, which is reported as 0.4-0.7 mM (pH 7, 25° C.) [S2-S4]. At these conditions, step advancement was observable at a reasonable timescale; however, supersaturated solutions with L-cystine concentrations three times solubility did not result in step growth during the time of measurement. At static conditions, solute is depleted from solution during growth, leading to a slight decrease in the step velocity with increasing time. As such, the total number of crystals adhered to the sample disk were minimized to lower the total surface area of crystals exposed to the growth solution, thereby minimizing depletion of solute. Topographical images were acquired at maximal integral and proportional gains (i.e. without feedback) using a scan rate of 5.1 Hz (256 samples per line) and a scan area of 5×5 µm². Crystal growth on the (0001) surface was measured as the distance a step advanced with time using consecutive deflection images where the acquisition time for each complete scan was approximately 50 sec.

AFM In Situ Growth

Figure 8:
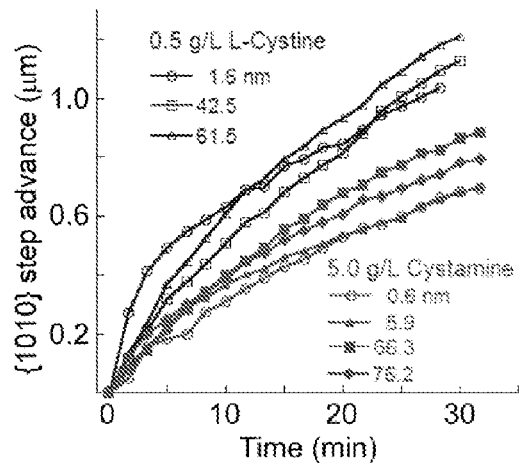
FIG. 8 depicts the rate of L-cystine crystal growth in the absence and presence of growth inhibitor L-cystamine, as measured with atomic force microscopy. Crystal growth in supersaturated L-cystine solutions (0.5 g/L) was measured at 25° C. in real time using AFM to monitor the advancement of steps on the (0001) surface. Measurements were performed at static conditions (i.e. no continuous flow of solute). The step velocity was calculated by linear regression analysis of step advancement for data after 10 min of growth. Step velocity in the absence of cystamine (blue) and in the presence of 5 g/L cystamine (red) is ~29 nm/min and 18±3 nm/min, respectively. Data for various step heights reveal that step velocity is independent of step height.

Potential molecular growth inhibitors that structurally mimic L-cystine, but differ in functionality (Scheme 1), were used in this investigation to examine their influence on step advancement. AFM in situ growth measurements in real time monitor the advancement of {1010} steps on hexagonal L-cystine surfaces in both the absence and presence of additives. Growth measurements in 5 g/L cystamine solutions (FIG. 8) reveal that cystamine reduces step velocity by 36% relative to the control (i.e. blue data). Investigations of L-cystine growth in the presence of other additives (identified in Table 1) had negligible effects on step velocity, with the exception of CDME which is reported herein.

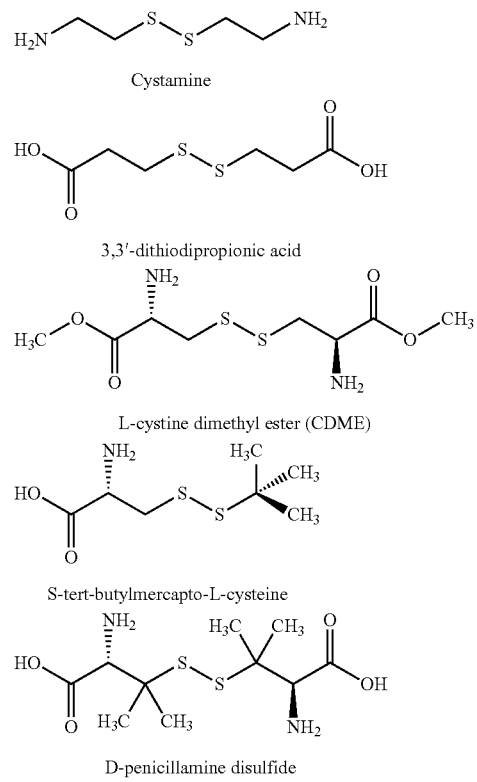

Scheme 1: Growth Inhibitors that Structurally Mimic L-Cystine

Cystamine 3,3'-dithiodipropionic acid

L-cystine dimethyl ester (CDME)

S-tert-butylmercapto-L-cysteine

D-penicillamine disulfide

Influence of Additives on L-Cystine Crystal Yield

L-cystine bulk crystallization was investigated in the presence of various polymers, urinary constituents, fish antifreeze proteins (AFPs), and L-cystine derivatives (i.e. structural mimics of L-cystine), which were analyzed as possible growth inhibitors of hexagonal L-cystine. The potency of each additive was assessed by comparing the difference in crystal yield (Table 1), which is equal to the mass of crystals formed in the presence of 2 mg/L additive (isolated with 11 mm-pore filters) divided by the total mass of L-cystine (700 mg/L). It should be noted that yields account for crystals >11 µm (i.e. those too large to pass through the filter), which is much smaller than the minimum size (~50 µm) observed in optical micrographs of hexagonal platelets.

TABLE 1

Mass Yields from Bulk Crystallization Experiments

| Additives | Compound[1] | Yield (%)[2,3] |
|---|---|---|
| Polymers | Poly(acrylic acid) | 39 |
|  | Poly-L-aspartate[4] | 44 |
|  | Poly-L-glutamate | 56 |
|  | Poly-L-lysine[4] | 64 |
|  | Poly-L-arginine[4] | 34 |

TABLE 1-continued

Mass Yields from Bulk Crystallization Experiments

| Additives | Compound[1] | Yield (%)[2,3] |
|---|---|---|
| Urinary Constituents | Human serum albumin | 63 |
| | Osteopontin (bovine) | 52 |
| | Transferrin | 56 |
| | Tamm-Horsfall protein | 69 |
| | Desialylated Tamm-Horsfall protein | 41 |
| | Chondroitin sulfate | 64 |
| | Citrate | 74 |
| Anti-Freeze Proteins | AFP Type I[4] | 31 |
| | AFP Type III[4] | 35 |
| L-Cystine Derivatives | Cystamine[4] | 30 |
| | 3,3'-Dithiodiproprionic acid[4] | 72 |
| | L-cystine dimethyl ester[4] | 13* |
| | S-tert-butylmercapto-L-cystine[4] | 45 |
| | D-penicillamine disulfide | 65 |
| | L-cystine methyl ester | 92* |
| L-Cysteine/Derivatives | L-cysteine[5] | 91 |
| | L-cysteine methyl ester[5] | 32 |
| No Additive | NA | 80 |

[1]Solutions were composed of 2 mg/L additive and 0.7 g/L L-cystine (pH 6.8)
[2]Yield = (collected mass by filtration, >11 μm)/(total mass added) × 100%
[3]Yields have an approximate error of ±8% (average of 3 repeat measurements)
[4]Additives employed for in AFM growth measurements
[5]Solutions were composed of 10 mg/L additive and 0.7 g/L L-cystine Crystal yield in 700 mg/L L-cystine (without additive) is 80±8%. The majority of additives reduce yields to 40-75%, suggesting that additives in Table 1 have some degree of influence on crystallization. A small fraction of additives exhibited yields of <40%, such as AFPs types I and III, poly(acrylic acid), poly-L-arginine, and L-cysteine methyl ester. Surprisingly, additives rich in carboxylate or amine groups that mimic functional groups in L-cystine had minimal influence on mass yield. CDME has the most pronounced effect on yield (13%), which qualitatively agrees with optical and SEM images which reveal crystal size is dramatically reduced in the presence of CDME.

EXEMPLARY COMPOUNDS OF THE INVENTION

The following compounds, as exemplified in Table 2, have been purchased or can be prepared according to the general synthetic methods known to one skilled in the art of organic synthesis. These compounds are or can be tested for their crystal growth inhibitory activity.

TABLE 2

Exemplary Compounds of the Invention*

Vd: $R^{1a}$–O–C(O)–CH(NH$_2$)–CH$_2$–S–S–CH$_2$–CH(NH$_2$)–C(O)–O–$R^{1b}$

| ID | Compound | $R^{1a}$ | $R^{1b}$ |
|---|---|---|---|
| 1 | L-CME | Me | H |
| 2 | L-CDME | Me | Me |
| 3 | L-CDEE | Et | Et |
| 4 | L-CDIE | i-Pr | i-Pr |
| 5 | L-CDTE | t-Bu | t-Bu |

*additional data in FIGS. 16, 17 and 18.

The data presented herein show that L-cystine alkyl esters are effective growth inhibitors for L-cystine crystallization.

X-Ray Diffraction

There are four reported crystal structures of L-cystine having hexagonal, tetragonal, and monoclinic structures. Single crystal X-ray diffraction (SCXRD) measurements of L-cystine crystals yielded unit cell parameters that agree with reported structural data (Table 2). SCXRD analysis of CDME needles agrees with structural data in the literature. The small size of L-cystine tetragonal needles required a synchrotron X-ray source to obtain the unit cell parameters.

TABLE 3

Comparison of Crystal Unit Cell Parameters

| Compound | Ref | Space Group | Unit Cell Parameters (Å) a | b | c | Cell Angles (deg) α | β | γ | Volume (Å³) |
|---|---|---|---|---|---|---|---|---|---|
| $C_6H_{14}N_2O_4S_2^{2+}$ 2(Cl$^-$) | [S5] | C2 | 18.6 | 5.3 | 7.2 | 90 | 103.6 | 90 | 687 |
| | OW | | 18.5 | 5.2 | 7.3 | 90 | 104.1 | 90 | 678 |
| $C_6H_{14}N_2O_4S_2^{2+}$2(Cl$^-$)2(H$_2$O) | [S6] | P2$_1$ | 5.9 | 13.2 | 9.4 | 90 | 90.8 | 90 | 728 |
| | OW | | 5.9 | 13.2 | 9.3 | 90 | 90.6 | 90 | 717 |
| $C_6H_{12}N_2O_4S_2$ (Hexagonal) | [S7] | P6$_1$22 | 5.4 | 5.4 | 56.2 | 90 | 90 | 120 | 1433 |
| | OW | | 5.4 | 5.4 | 57.0 | 90 | 90 | 120 | 1455 |
| $C_6H_{12}N_2O_4S_2$ | [S8] | P4$_1$ | 6.7 | 6.7 | 21.7 | 90 | 90 | 90 | 978 |
| | OW | | 6.7 | 6.7 | 21.6 | 90 | 90 | 90 | 971 |
| $C_8H_{14}N_2O_4S_2^{2+}$ 2(Cl$^-$)H$_2$O | [S9] | P2$_1$ | 5.9 | 9.3 | 14.8 | 90 | 91.5 | 90 | 808 |
| | OW | | 5.9 | 9.1 | 14.9 | 90 | 91.6 | 90 | 831 |

[5] Steinrauf et al.,
[6] Kominami et al.,
[7] Oughton et al.,
[8] Chaney et al.,
[9] Vijayalakshmi et al.;
OW = Our work Powder X-ray diffraction (XRD) analyses of tetragonal L-cystine needles, L-cystine dihydrochloride, and CDME are compared in FIG. 14. Small quantities of needles (50-100 mg) resulted in significant background scattering from the sample holder, as revealed by broad peaks over the range of 2θ=15-40 degrees.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds given in this application were generated using various commercially available chemical naming software tools including MDL's ISIS Draw Autonom Software tool, and were not verified. Particularly, in the event of inconsistency, the depicted structure governs.

REFERENCES

1. Dolin, D. J., et al. *J. Endourology*, 2005. 19(3): 429-432.
2. Mattoo, A. and Goldfarb, D. S. *Seminars in Nephrology*, 2008. 28(2): 181-191.
3. Moe, O. W. *Lancet*, 2006. 367(9507): 333-344.
4. Becker, G. *Nephrology*, 2007. 12: S4-S10.
5. Nakagawa, Y., et al. *J. Urol.*, 2000. 164(5): 1481-1485.
6. Moggach, S. A., et al. *J. Synchrotron Radiation*, 2005. 12: 598-607.
7. Dahaoui, S., Pichon-Pesme, V., Howard, J. A. K., and Lecomte, C. *J. Phys. Chem. A*, 1999. 103(31): 6240-6250.
8. Girija, E. K., Kalkura, S. N., and Ramasamy, P. *J. Mater. Sci. Mater. Med.*, 1995. 6(11): 617-619.
9. Fujiki, Y., Tokunaga, N., Shinkai, S., and Sada, K. *Angew. Chem. Int. Ed.*, 2006. 45(29): 4764-4767.
10. Chaney, M. O. and Steinrau. Lk. *Acta Cryst. B*, 1974. B 30(March 15): 711-716.
11. Steinrauf, L. K., Peterson, J., and Jensen, L. H. *J. Amer. Chem. Soc.*, 1958. 80(15): 3835-3838.
12. Kominami; S., Riesz, P., Akiyama, T., and Silverton, J. V. *J. Phys. Chem.*, 1976. 80(2): 203-210.
13. Carta, R. and Tola, G. *J. Chem. Eng. Data*, 1996. 41(3): 414-417.
14. Kuzmenko, I., et al. *Science*, 1996. 274(5295): 2046-2049.
15. Weinbach, S. P., et al. *Science*, 1994. 264(5165): 1566-1570.
16. Weissbuch, I., Addadi, L., Lahav, M., and Leiserowitz, L. *Science*, 1991. 253(5020): 637-645.
17. Graether, S. P., et al. *Nature*, 2000. 406(6793): 325-328.
18. Graham, L. A. and Davies, P. L. *Science*, 2005. 310(5747): 461-461.
19. Liou, Y. C., Tocilj, A., Davies, P. L., and Jia, Z. C. *Nature*, 2000. 406(6793): 322-324.
20. Sonnichsen, F. D., Sykes, B. D., Chao, H., and Davies, P. L. *Science*, 1993. 259(5098): 1154-1157.
21. Orme, C. A., et al. *Nature*, 2001. 411(6839): 775-779.
22. Stephenson, A. E., et al. *Science*, 2008. 322(5902): 724-727.
23. Sheng, X. X., Jung, T. S., Wesson, J. A., and Ward, M. D. *Proc. Nat. Acad. Sci. U.S.A.*, 2005. 102(2): 267-272.
24. DeYoreo, J. J. and Dove, P. M. *Science*, 2004. 306(5700): 1301-1302.
25. Grohe, B., et al. *J. Am. Chem. Soc.*, 2007. 129(48): 14946-14951.
26. Sizemore, J. P. and Doherty, M. F. *Cryst. Growth Des.*, 2009. 9(6): 2637-2645.
27. Jung, T., et al. *Langmuir*, 2004. 20(20): 8587-8596.
28. Kessler, A., et al. *Neurochem. Res.*, 2008. 33(5): 737-744.
29. Wilmer, M. J., et al. *Pediatric Res.*, 2007. 62(2): 151-155.
30. Foreman, et al. *Metabolism Clin. & Experimental*, 1987. 36(12): 1185-1191.
S1. Fujiki, Y., Tokunaga, N., Shinkai, S., and Sada, K. *Angew. Chem. Int. Ed.*, 2006. 45(29): 4764-4767.
S2. Carta, R. and Tola, G. *J. Chem. Eng. Data*, 1996. 41(3): 414-417.
S3. Kallistratos, G. and Malorny, G. *Arzneimittel-Forschung*, 1972. 22(9): 1434-&.
S4. Konigsberger, E., Wang, Z. H., and Konigsberger, L. C. *Monatshefte Fur Chemie*, 2000. 131(1): 39-45.
S5. Steinrauf, L. K., Peterson, J., and Jensen, L. H. *J. Amer. Chem. Soc.*, 1958. 80(15): 3835-3838.
S6. Kominami, S., Riesz, P., Akiyama, T., and Silverton, J. V. *J. Phys. Chem.*, 1976. 80(2): 203-210.
S7. Oughton, B. M. and Harrison, P. M. *Acta Crystallographica*, 1959. 12(5): 396-404.
S8. Chaney, M. O. and Steinrau. Lk. *Acta Cryst. B*, 1974. B 30(March 15): 711-716.
S9. Vijayalakshmi, B. K. and Srinivasan, R. *Acta Cryst. B*, 1975. B 31(April 15): 993-998.
S10. Eldjarn, L. and Hambraeus, L. *Scand. J. Clin. Lab. Invest.*, 1964. 16(2): 153-&.
S11. Theriault, Y. and Rabenstein, D. L. *Canadian J. Chem.*, 1985. 63(8): 2225-2231.

What is claimed is:

1. A method for inhibiting or slowing the growth of L-cystine crystallization in a subject where such growth is present comprising administering to the subject an effective amount of a compound of formula III:

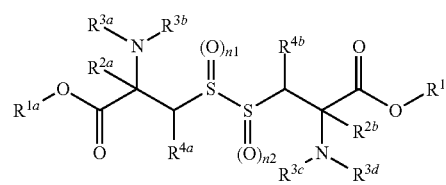

or a pharmaceutically acceptable salt, solvate, or prodrug thereof, and stereoisomers, tautomers and isotopic variants thereof; and wherein each $R^{1a}$ and $R^{1b}$ is independently selected from H, alkyl, alkenyl, alkynyl, and cycloalkyl;

each $R^{2a}$, $R^{2b}$, $R^{3a}$, $R^{3b}$, $R^{3c}$, $R^{3d}$, $R^{4a}$, and $R^{4b}$ is independently selected from H, and alkyl; and each n1 and n2 is independently 0, 1, or 2;

provided that when each n1 and n2 is 0, then at least one of $R^{1a}$ and $R^{1b}$ is other than H.

2. The method of claim 1, wherein each of $R^{2a}$ and $R^{2b}$ is H.
3. The method of claim 1, wherein one of $R^{2a}$ and $R^{2b}$ is H; and the other is alkyl.
4. The method of claim 1, wherein each of $R^{2a}$ and $R^{2b}$ is alkyl.
5. The method of claim 1, wherein each of $R^{3a}$ and $R^{3b}$ is H.
6. The method of claim 1, wherein one of $R^{3b}$ and $R^{3b}$ is H; and the other is alkyl.
7. The method of claim 1, wherein each of $R^{3a}$ and $R^{3b}$ is alkyl.
8. The method of claim 1, wherein each of $R^{3c}$ and $R^{3d}$ is H.
9. The method of claim 1, wherein one of $R^{3c}$ and $R^{3d}$ is H; and the other is alkyl.
10. The method of claim 1, wherein each of $R^{3c}$ and $R^{3d}$ is alkyl.

11. The method of claim 1, wherein each of $R^{4a}$ and $R^{4b}$ is H.

12. The method of claim 1, wherein one of $R^{4a}$ and $R^{4b}$ is H; and the other is alkyl.

13. The method of claim 1, wherein each of $R^{4a}$ and $R^{4b}$ is alkyl.

14. The method of claim 1, wherein one of $R^{1a}$ and $R^{1b}$ is H; and the other is alkyl.

15. The method of claim 1, wherein one of $R^{1a}$ and $R^{1b}$ is H; and the other is alkenyl.

16. The method of claim 1, wherein one of $R^{1a}$ and $R^{1b}$ is H; and the other is alkynyl.

17. The method of claim 1, wherein one of $R^{1a}$ and $R^{1b}$ is H; and the other is cycloalkyl.

18. The method of claim 1, wherein each of $R^{1a}$ and $R^{1b}$ is alkyl.

19. The method of claim 1, wherein each of $R^{1a}$ and $R^{1b}$ is alkenyl.

20. The method of claim 1, wherein each of $R^{1a}$ and $R^{1b}$ is alkynyl.

21. The method of claim 1, wherein each of $R^{1a}$ and $R^{1b}$ is cycloalkyl.

22. A method for inhibiting or slowing the growth of L-cystine kidney-stone formation in a subject in need thereof, the method comprising administering a pharmaceutically effective amount to the subject a compound of formula III:

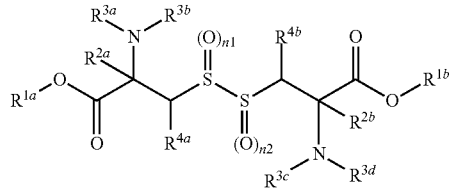

III or a pharmaceutically acceptable salt, solvate or prodrug thereof, and stereoisomers, tautomers and isotopic variants thereof; and wherein each $R^{1a}$ and $R^{1b}$ is independently selected from H, alkyl, alkenyl, alkynyl, and cycloalkyl; each $R^{2a}$, $R^{2b}$, $R^{3a}$, $R^{3b}$, $R^{3c}$, $R^{3d}$, $R^{4a}$, and $R^{4b}$ is independently selected from H, and alkyl; and each n1 and n2 is independently 0, 1, or 2; provided that when each n1 and n2 is 0, then at least one of $R^{1a}$ and $R^{1b}$ is other than H.

23. A method of treating a subject having chronic kidney disease, comprising administering to a subject in need thereof a pharmaceutically effective amount of a compound of formula III:

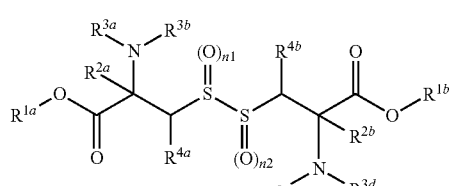

III or a pharmaceutically acceptable salt, solvate or prodrug thereof, and stereoisomers, tautomers and isotopic variants thereof; and wherein each $R^{1a}$ and $R^{1b}$ is independently selected from H, alkyl, alkenyl, alkynyl, and cycloalkyl; each $R^{2a}$, $R^{2b}$, $R^{3a}$, $R^{3b}$, $R^{3c}$, $R^{3d}$, $R^{4a}$, and $R^{4b}$ is independently selected from H, and alkyl; and each n1 and n2 is independently 0, 1, or 2; provided that when each n1 and n2 is 0, then at least one of $R^{1a}$ and $R^{1b}$ is other than H.

24. The method according to claim 23, wherein the subject is human.

25. A method for reducing a L-cystine crystal concentration in a human or animal comprising administering to a human or animal in need thereof a pharmaceutically effective amount of a compound of formula III:

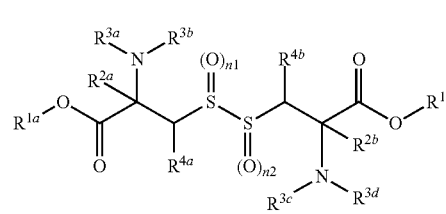

III or a pharmaceutically acceptable salt, solvate or prodrug thereof, and stereoisomers, tautomers and isotopic variants thereof; and wherein each $R^{1a}$ and $R^{1b}$ is independently selected from H, alkyl, alkenyl, alkynyl, and cycloalkyl; each $R^{2a}$, $R^{2b}$, $R^{3a}$, $R^{3b}$, $R^{3c}$, $R^{3d}$, $R^{4a}$, and $R^{4b}$ is independently selected from H, and alkyl; and each n1 and n2 is independently 0, 1, or 2; provided that when each n1 and n2 is 0, then at least one of $R^{1a}$ and $R^{1b}$ is other than H.

26. A method for treating a L-cystine crystal related condition in a human or animal comprising administering to a human or animal in need thereof a pharmaceutically effective amount of a compound of formula III:

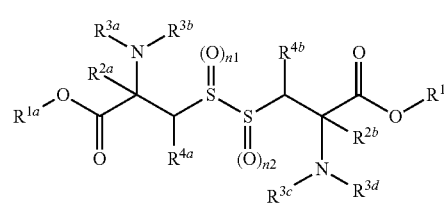

III or a pharmaceutically acceptable salt, solvate or prodrug thereof, and stereoisomers, tautomers and isotopic variants thereof; and wherein each $R^{1a}$ and $R^{1b}$ is independently selected from H, alkyl, alkenyl, alkynyl, and cycloalkyl; each $R^{2a}$, $R^{2b}$, $R^{3a}$, $R^{3b}$, $R^{3c}$, $R^{3d}$, $R^{4a}$, and $R^{4b}$ is independently selected from H, and alkyl; and each n1 and n2 is independently 0, 1, or 2; provided that when each n1 and n2 is 0, then at least one of $R^{1a}$ and $R^{1b}$ is other than H.

27. The method of claim 8, wherein each $R^{2a}$, $R^{2b}$, $R^{3a}$, $R^{3b}$, $R^{3c}$, $R^{3d}$, $R^{4a}$, and $R^{4b}$ is H; and each n1 and n2 is 0; or each n1 and n2 is 1; or each n1 and n2 is 2.

28. The method of claim 1, wherein each $R^{2a}$, $R^{2b}$, $R^{3a}$, $R^{3b}$, $R^{3c}$, $R^{3d}$, $R^{4a}$, and $R^{4b}$ is H; each n1 and n2 is 0; or each n1 and n2 is 1; or each n1 and n2 is 2; and one of $R^{1a}$ and $R^{1b}$ is H; and the other is Me or Et.

29. The method of claim 8, wherein each $R^{2a}$, $R^{2b}$, $R^{3a}$, $R^{3b}$, $R^{3c}$, $R^{3d}$, $R^{4a}$, and $R^{4b}$ is H; each n1 and n2 is 0; or each n1 and n2 is 1; or each n1 and n2 is 2; and each of $R^{1a}$ and $R^{1b}$ is Me.

30. The method of claim 8, wherein each $R^{2a}$, $R^{2b}$, $R^{3a}$, $R^{3b}$, $R^{3c}$, $R^{3d}$, $R^{4a}$, and $R^{4b}$ is H; each n1 and n2 is 0; and each of $R^{1a}$ and $R^{1b}$ is Et.

31. The method of claim 1, wherein the compound is cystine methyl ester, cystine dimethyl ester, cystine diethyl ester, cystine di-isopropyl ester, or cystine di-t-butyl ester.

\* \* \* \* \*